US012048919B2

(12) United States Patent
Román-Leshkov et al.

(10) Patent No.: US 12,048,919 B2
(45) Date of Patent: Jul. 30, 2024

(54) CATALYTIC COMPOSITIONS FOR THE OXIDATION OF SUBSTRATES

(71) Applicants: Massachusetts Institute of Technology, Cambridge, MA (US); ExxonMobil Technology and Engineering Company, Annandale, NJ (US)

(72) Inventors: Yuriy Román-Leshkov, Cambridge, MA (US); Randall J. Meyer, Clinton, NJ (US); Pedro M. Serna Merino, Branchburg, NJ (US); Mark Sullivan, Midland, MI (US); Kimberly Dinh, Midland, MI (US)

(73) Assignees: Massachusetts Institute of Technology, Cambridge, MA (US); ExxonMobil Research and Engineering Company, Annandale, NJ (US)

( * ) Notice: Subject to any disclaimer, the term of this patent is extended or adjusted under 35 U.S.C. 154(b) by 263 days.

(21) Appl. No.: 17/217,782

(22) Filed: Mar. 30, 2021

(65) Prior Publication Data

US 2021/0346875 A1 Nov. 11, 2021
US 2022/0314207 A9 Oct. 6, 2022

Related U.S. Application Data

(60) Provisional application No. 63/029,751, filed on May 26, 2020, provisional application No. 63/002,415, filed on Mar. 31, 2020.

(51) Int. Cl.
| | | |
|---|---|---|
| *B01J 29/072* | (2006.01) | |
| *B01J 29/00* | (2006.01) | |
| *B01J 29/06* | (2006.01) | |
| *B01J 29/24* | (2006.01) | |
| *B01J 29/40* | (2006.01) | |
| *B01J 29/68* | (2006.01) | |
| *B01J 29/76* | (2006.01) | |
| *B01J 29/80* | (2006.01) | |
| *B01J 29/83* | (2006.01) | |
| *B01J 29/86* | (2006.01) | |
| *B01J 29/87* | (2006.01) | |

(Continued)

(52) U.S. Cl.
CPC ........... *B01J 29/763* (2013.01); *B01J 29/005* (2013.01); *B01J 29/061* (2013.01); *B01J 29/072* (2013.01); *B01J 29/24* (2013.01); *B01J 29/40* (2013.01); *B01J 29/68* (2013.01); *B01J 29/7615* (2013.01); *B01J 29/80* (2013.01); *B01J 29/83* (2013.01); *B01J 29/86* (2013.01); *B01J 29/87* (2013.01); *B01J 37/0036* (2013.01); *B01J 37/0063* (2013.01); *B01J 37/04* (2013.01); *C07C 29/48* (2013.01); *B01J 2029/062* (2013.01); *B01J 2229/18* (2013.01); *B01J 2229/183* (2013.01); *B01J 2229/186* (2013.01); *B01J 2229/20* (2013.01); *C07C 2529/06* (2013.01); *C07C 2529/072* (2013.01); *C07C 2529/24* (2013.01); *C07C 2529/40* (2013.01); *C07C 2529/68* (2013.01); *C07C 2529/70* (2013.01); *C07C 2529/76* (2013.01); *C07C 2529/80* (2013.01); *C07C 2529/83* (2013.01); *C07C 2529/85* (2013.01); *C07C 2529/87* (2013.01)

(58) Field of Classification Search
CPC ...... B01J 29/005; B01J 29/061; B01J 29/072; B01J 29/763; B01J 29/40; B01J 29/80; B01J 29/68; B01J 29/24; B01J 29/7615; B01J 29/7623; B01J 29/83; B01J 29/86; B01J 29/87; B01J 2029/062; B01J 2229/18; B01J 2229/183; B01J 2229/186; B01J 2229/20; B01J 35/002; B01J 35/0006; B01J 37/04; B01J 37/0036; B01J 37/0063; Y02P 20/52; C07C 2529/40; C07C 2529/06; C07C 2529/072; C07C 2529/24; C07C 2529/68; C07C 2529/70; C07C 2529/76; C07C 2529/80; C07C 2529/83; C07C 2529/85; C07C 2529/86; C07C 2529/87
USPC ........ 502/60, 61, 63, 64, 66, 67, 69, 71, 74, 502/77, 78
See application file for complete search history.

(56) References Cited

U.S. PATENT DOCUMENTS

| | | | |
|---|---|---|---|
| 3,702,886 | A | 11/1972 | Argauer et al. |
| 4,503,023 | A | 3/1985 | Breck et al. |

(Continued)

FOREIGN PATENT DOCUMENTS

| | | | |
|---|---|---|---|
| WO | WO 2011/046621 | A1 | 4/2011 |
| WO | WO 2016/065034 | * | 4/2016 |

OTHER PUBLICATIONS

Alayon et al., Catalytic conversion of methane to methanol over Cu-mordenite. Chemical Communications. 2012;48:404-6. Epub Nov. 11, 2011.

(Continued)

*Primary Examiner* — Elizabeth D Wood
(74) *Attorney, Agent, or Firm* — Wolf, Greenfield & Sacks, P.C.

(57) ABSTRACT

Catalytic compositions and sequential catalytic methods are generally described. In some embodiments, a composition comprises a first catalyst comprising a Cu-modified zeolite, and a second catalyst capable of a coupling reaction between (a) an intermediate resulting from a reaction of a reactant at the first catalyst, and (b) a co-reagent, wherein a rate of diffusion of the co-reagent within one or more cages and/or pores of the first catalyst is lower than a rate of diffusion of the intermediate within the one or more cages and/or pores of the first catalyst.

20 Claims, 19 Drawing Sheets

(51) Int. Cl.
    *B01J 37/00*     (2006.01)
    *B01J 37/04*     (2006.01)
    *C07C 29/48*     (2006.01)

(56)             References Cited

U.S. PATENT DOCUMENTS

| | | | |
|---|---|---|---|
| 4,661,467 | A | 4/1987 | Kuehl |
| 4,665,249 | A | 5/1987 | Mao et al. |
| 5,345,011 | A | 9/1994 | Durante et al. |
| 10,099,979 | B2 | 10/2018 | Roman-Leshkov et al. |
| 2005/0203323 | A1 | 9/2005 | Harris et al. |
| 2007/0270512 | A1 | 11/2007 | Edwards |
| 2008/0249197 | A1 | 10/2008 | Bricker et al. |
| 2010/0280289 | A1 | 11/2010 | De Winne et al. |
| 2015/0118115 | A1* | 4/2015 | Chen .................. B01D 53/945 502/67 |
| 2016/0367937 | A1* | 12/2016 | Lu ........................ B01J 21/04 |

OTHER PUBLICATIONS

Alayon et al., Reaction Conditions of Methane-to-Methanol Conversion Affect the Structure of Active Copper Sites. ACS Catalysis. 2014;4(1):16-22. Epub Nov. 20, 2013.

Balasubramanian et al., Oxidation of methane by a biological dicopper centre. Nature. May 6, 2010;465:115-9. Epub Apr. 21, 2010.

Behrens et al., Active Site of Methanol Synthesis over Cu/ZnO/$Al_2O_3$ Industrial Catalysts. Science. May 18, 2012;336(6083):893-7.

Blaszkowski et al., The Mechanism of Dimethyl Ether Formation from Methanol Catalyzed by Zeolitic Protons. J. Am. Chem. Soc. 1996;118:5152-3. Epub May 29, 1996.

Caballero et al., Silver-Catalyzed C—C Bond Formation Between Methane and Ethyl Diazoacetate in Supercritical $CO_2$. Science. May 13, 2011;332(6031):835-8.

Camblor et al., Spontaneous nucleation and growth of pure silica zeolite-β free of connectivity defects. Chem. Commun. 1996;20:2365-6.

Cavaliere et al., Methane: a new frontier in organometallic chemistry. Chemical Science. 2012;3:3356-65. Epub Jul. 6, 2012.

Chang et al., Methanol conversion to olefins over ZSM-5: I. Effect of temperature and zeolite $SiO_2Al_2O_3$. Journal of Catalysis. Apr. 1984;86(2):289-96.

Chang et al., Process Studies on the Conversion of Methanol to Gasoline. Ind. Eng. Chem. Process Des. Dev. Jul. 1978;17(3):255-60.

Chen et al., Spatial confinement effects of cage-type SAPO molecular sieves on product distribution and coke formation in methanol-to-olefin reaction. Catalysis Communications. Feb. 10, 2014;46:36-40.

Dejaifve et al., Reaction pathways for the conversion of methanol and olefins on H-ZSM-5 zeolite. Journal of Catalysis. Jun. 1980;63(2):331-45.

Dinh et al., Continuous Partial Oxidation of Methane to Methanol Catalyzed by Diffusion-Paired Copper Dimers in Copper-Exchanged Zeolites. J Am Chem Soc. Jul. 24, 2019;141(29):11641-11650. doi: 10.1021/jacs.9b04906. Epub Jul. 15, 2019.

Ellis et al., Heterogeneous catalysts for the direct, halide-free carbonylation of methanol. Stud. Surf. Sci. Catal. 1996;101:771-9. Epub Oct. 14, 2008.

Gao et al., Understanding ammonia selective catalytic reduction kinetics over Cu/SSZ-13 from motion of the Cu ions. Journal of Catalysis. Nov. 2014;319:1-14. Epub Sep. 6, 2014.

Golisz et al., Chemistry in the Center for Catalytic Hydrocarbon Functionalization: An Energy Frontier Research Center. Catal Lett. Feb. 2011;141:213-21.

Gonçalves et al., Promoting Effect of Ce on the Oxidative Coupling of Methane Catalysts. Catalysis Letters. Mar. 2010;135(1-2):26-32.

Groothaert et al., Selective Oxidation of Methane by the Bis(μ-oxo)dicopper Core Stabilized on ZSM-5 and Mordenite Zeolites. J. Am. Chem. Soc. 2005;127(5):1394-5. Epub Jan. 15, 2005.

Grundner et al., Single-site trinuclear copper oxygen clusters in mordenite for selective conversion of methane to methanol. Nature Communications. 2015;6:7546. Epub Jun. 25, 2015. 9 pages.

Grundner et al., Synthesis of single-site copper catalysts for methane partial oxidation. Chem Commun. 2016;52:2553-6. Epub Dec. 24, 2015.

Hammond et al., Direct Catalytic Conversion of Methane to Methanol in an Aqueous Medium by using Copper-Promoted Fe-ZSM-5. Angewandte Chemie Int Ed. May 21, 2012;51(21):5129-33.

Hammond et al., Elucidation and Evolution of the Active Component within Cu/Fe/ZSM-5 for Catalytic Methane Oxidation: From Synthesis to Catalysis. ACS Catalysis. 2013;3(4):689-99. Epub Feb. 7, 2013.

Hammond et al., Oxidative Methane Upgrading. ChemSusChem. Sep. 2012;5(9):1668-86.

Hassanpour et al., Performance of modified H-ZSM-5 zeolite for dehydration of methanol to dimethyl ether. Fuel Processing Technology. Oct. 2010;91(10):1212-21.

Ito et al., Synthesis of ethylene and ethane by partial oxidation of methane over lithium-doped magnesium oxide. Nature. Apr. 25, 1985;314:721-2.

Khalilpour et al., Evaluation of utilization alternatives for stranded natural gas. Energy. Apr. 2012;40(1):317-28.

Kopp et al., Soluble methane monooxygenase: activation of dioxygen and methane. Current Opinion in Chemical Biology. Oct. 1, 2002;6(5):568-76.

Kosinov et al., Engineering of transition metal catalysts confined in zeolites. Chem Mater 2018. 30(10): 3177-98.

Kulkarni et al., Cation-exchanged zeolites for the selective oxidation of methane to methanol. Catal. Sci. Technol. 2018. 8(1): 114-23.

Latimer et al., Direct methane to methanol: the selectivity-conversion limit and design strategies. ACS Catal. 2018; 8:6894-907.

Lee et al., Structural and Functional Models of the Dioxygen-Activating Centers of Non-Heme Diiron Enzymes Ribonucleotide Reductase and Soluble Methane Monooxygenase. J. Am. Chem. Soc. 1998;120(46):12153-4. Epub Nov. 10, 1998.

Li et al., Hydrated Dibromodioxomolybdenum(VI) Supported on Zn-MCM-48 for Facile Oxidation of Methane. Angewandte Chemie Int Ed. 2006;45:6541-4. Epub Sep. 5, 2006.

Li et al., Stability and reactivity of copper oxo-clusters in ZSM-5 zeolite for selective methane oxidation to methanol. Journal of Catalysis. Jun. 2016;338:305-12.

Lieberman et al., Crystal structure of a membrane-bound metalloenzyme that catalyses the biological oxidation of methane. Nature. Mar. 10, 2005;434:177-82. Epub Jan. 26, 2005.

Lunsford, Catalytic conversion of methane to more useful chemicals and fuels: a challenge for the 21st century. Catalysis Today. Dec. 25, 2000;63(2-4):165-74.

Martínez-Franco et al., Rational direct synthesis methodology of very active and hydrothermally stable Cu-SAPO-34 molecular sieves for the SCR of $NO_x$. Applied Catalysis B: Environmental. Oct. 30, 2012;127:273-80.

Narsimhan et al., Catalytic Oxidation of Methane into Methanol over Copper-Exchanged Zeolites with Oxygen at Low Temperature. ACS Cent Sci. Jun. 22, 2016;2(6):424-9. doi: 10.1021/acscentsci.6b00139. Epub Jun. 13, 2016.

Ovanesyan et al., The state of iron in the Fe-ZSM-5-N2O system for selective oxidation of methane to methanol from data of Mössbauer spectroscopy. Kinet. Catal. 1998;39:792-7.

Palkovits et al., Solid Catalysts for the Selective Low-Temperature Oxidation of Methane to Methanol. Angewandte Chemie Int Ed. Sep. 1, 2009;48(37):6909-12.

Palomino et al., Oxidation States of Copper Ions in ZSM-5 Zeolites. A Multitechnique Investigation. J. Phys. Chem. B. 2000;104(17):4064-73. Epub Mar. 30, 2000.

Panov et al., Iron complexes in zeolites as a new model of methane monooxygenase. React Kinet Catal Lett. 1997. 61(2): 251-8.

(56) References Cited

OTHER PUBLICATIONS

Panov et al., Iron complexes in zeolites as a new model of methane monooxygenase. Reaction Kinetics and Catalysis Letters. Jul. 1997;61(2):251-8.

Periana et al., A Mercury-Catalyzed, High-Yield System for the Oxidation of Methane to Methanol. Science. Jan. 15, 1993;259(5093):340-3.

Periana et al., Platinum Catalysts for the High-Yield Oxidation of Methane to a Methanol Derivative. Apr. 24, 1998;280(5363):560-4.

Persson et al., The synthesis of discrete colloidal particles of TPA-silicalite-1. Zeolites. Sep.-Oct. 1994;14(7):557-67.

Ren et al., Designed copper-amine complex as an efficient template for one-pot synthesis of Cu-SSZ-13 zeolite with excellent activity for selective catalytic reduction of $NO_x$ by $NH_3$. Chemical Communications. 2011;47:9789-91. Epub May 31, 2011.

Sajith et al., Role of Acidic Proton in the Decomposition of NO over Dimeric Cu(I) Active Sites in Cu-ZSM-5 Catalyst: A QM/MM Study. ACS Catalysis. 2014;4(6):2075-85. Epub May 15, 2014.

Shu et al., An $Fe_2^{IV} NO_2$ Diamond Core Structure for the Key Intermediate Q of Methane Monooxygenase. Science. Jan. 24, 1997;275(5299):515-8.

Silva et al., Insights to achieve a better control of silicon-aluminum ratio and ZSM-5 zeolite crystal morphology through the assistance of biomass. Catal. 2016; 6(30): 1-10.

Smeets et al., Cu based zeolites: A UV-vis study of the active site in the selective methane oxidation at low temperatures. Catalysis Today. Dec. 30, 2005;110(3-4):303-9.

Smith et al., Catalytic borylation of methane. Science. Mar. 25, 2016;351(6280):1424-7.

Snyder et al., Iron and copper active sites in zeolites and their correlation to metalloenzymes. Chem Rev 2018. 118(5); 2718-68.

Song et al., A high performance oxygen storage material for chemical looping processes with $CO_2$ capture. Energy Environ. Sci. 2013;6:288-98. Epub Nov. 22, 2012.

Sunley et al., High productivity methanol carbonylation catalysis using iridium: The Cativa™ process for the manufacture of acetic acid. Catalysis Today. May 26, 2000;58(4):293-307.

Szécsényi et al., Mechanistic complexity of methane oxidation with H2O2 by single-site Fe/ZSM-5 catalyst. ACS Catal. 2018. 8(9): 7961-72.

Thomas et al., Review of ways to transport natural gas energy from countries which do not need the gas for domestic use. Energy. Nov. 2003;28(14):1461-77.

Tomkins et al., Isothermal Cyclic Conversion of Methane into Methanol over Copper-Exchanged Zeolite at Low Temperature. Angewandte Chemie Int Ed. 2016;55:5467-71. Epub Mar. 24, 2016.

Unruh et al., Fischer-Tropsch Synfuels from Biomass: Maximizing Carbon Efficiency and Hydrocarbon Yield. Energy Fuels. 2010;24(4):2634-41. Epub Mar. 30, 2010.

Vanelderen et al., Cu-ZSM-5: A biomimetic inorganic model for methane oxidation. Journal of Catalysis. Dec. 1, 2011;284(2):157-64.

Vanelderen et al., Spectroscopic Definition of the Copper Active Sites in Mordenite: Selective Methane Oxidation. J. Am. Chem. Soc. 2015;137(19):6383-92. Epub Apr. 26, 2015.

Vishwanathan et al., Vapour phase dehydration of crude methanol to dimethyl ether over Na-modified H-ZSM-5 catalysts. Applied Catalysis A: General. Nov. 25, 2004;276(1-2):251-5.

Wang et al., Role of Surface Methoxy Species in the Conversion of Methanol to Dimethyl Ether on Acidic Zeolites Investigated by in Situ Stopped-Flow MAS NMR Spectroscopy. J. Phys. Chem. B. 2001;105(50):12553-8. Epub Nov. 21, 2001.

Woertink et al., A [Cu2O]2+ core in Cu-ZSM-5, the active site in the oxidation of methane to methanol. Proc Natl Acad Sci U S A. Nov. 10, 2009;106(45):18908-13. doi: 10.1073/pnas.0910461106. Epub Oct. 28, 2009.

Wulfers et al., Conversion of methane to methanol on copper-containing small-pore zeolites and zeotypes. Chem. Comm. 2015;21:4447-50. Epub Feb. 4, 2015.

Yaripour et al., Catalytic dehydration of methanol to dimethyl ether (DME) over solid-acid catalysts. Catalysis Communications. Feb. 2005;6(2):147-52.

Corma, Inorganic Solid Acids and Their Use in Acid-Catalyzed Hydrocarbon Reactions. Chem Rev. 1995;95:559-614.

Bhan et al., Specificity of sites within eight-membered ring zeolite channels for carbonylation of methyls to acetyls. J Am Chem Soc. Apr. 25, 2007;129(16):4919-24.

Bozbag et al., Methane to methanol over copper mordenite: yield improvement through multiple cycles and different synthesis techniques. Catal. Sci. Technol. 2016, 6 (13), 5011-5022.

Carpenter et al., Further investigations of constraint index texting of zeolites that contain cases. J Catal. Jan. 2010; 269(1): 64-70.

Dusselier et al., Small-Pore Zeolites: Synthesis and Catalysis. Chem. Rev. 2018, 118 (11), 5265-5329.

Huang et al., Low-Temperature Transformation of Methane to Methanol on Pd1O4 Single Sites Anchored on the Internal Surface of Microporous Silicate. Angew. Chem. 2016, 128 (43), 13639-13643.

Ipek et al., Formation of [Cu2O2]2+ and [Cu2O]2+ toward C—H Bond Activation in Cu-SSZ-13 and Cu-SSZ-39. ACS Catal. 2017, 7 (7), 4291-4303.

Kulkarni et al, Monocopper active site for partial methane oxidation in Cu-Exchanged 8MR zeolites. ACS Catal. Aug. 17, 2016; 6(10): 6531-6.

Mayhuddin et al., Methane Partial Oxidation over [Cu2(µ-O)]2+ and [Cu3(µ-O)3]2+ Active Species in Large-Pore Zeolites. ACS Catal. 2018; 8(2): 1500-9.

Shan et al., Mild oxidation of methane to methanol or acetic acid on supported isolated rhodium catalysts. Nature 2017, 551 (7682), 605-608.

Vanelderen et al., Coordination chemistry and reactivity of copper in zeolites. Coord. Chem. Rev. 2013, 257 (2), 483-494.

* cited by examiner

| Catalyst | Temperature (K) | Pressure (bar) | Space Velocity ($g_{cat}$(mol min$^{-1}$)$^{-1}$) | CH$_4$ Conversion (%) | Toluene + Xylene Selectivity[d] (%) | Product Yield[d] ($\mu$mol min$^{-1}$ $g_{Cu-CHA}^{-1}$) |
|---|---|---|---|---|---|---|
| Cu-CHA-1/ H-MFI-2 | 543 | 1 | 329 | 0.004 | 70 | 0.06 |
|  | 573 | 1 | 329 | 0.009 | 100 | 0.19 |
|  | 603 | 1 | 329 | 0.023 | 98 | 0.48 |
|  | 633 | 1 | 329 | 0.054 | 85 | 0.98 |
|  | 663 | 1 | 329 | 0.099 | 77 | 1.64 |
|  | 543 | 11 | 329 | 0.039 | 89 | 0.68 |
|  | 543 | 11 | 329 | 0.022 | 89 | 1.13 |
|  | 543 | 1 | 329 | 0.004 | 77 | 0.06 |
|  | 543 | 1 | 163 | 0.003 | 72 | 0.08 |
|  | 543 | 1 | 81 | 0.002 | 64 | 0.09 |
|  | 543 | 1 | 41 | 0.001 | 51 | 0.11 |
| Cu-CHA-2/ H-MFI-3 | 543 | 1 | 329 | 0.003 | 69 | 0.06 |
|  | 543 | 11 | 329 | 0.034 | 88 | 0.72 |
|  | 543 | 11 | 1372 | 0.085 | 97 | 0.91 |
|  | 603[b] | 11 | 1372 | 0.37 | 80 | 1.74 |
|  | 603[c] | 11 | 1372 | 0.66 | 59 | 2.70 |

[a] Reactant feed composition: $x_{CH4}$ = 0.18, $x_{C6H6}$ = 0.008, $x_{O2}$ = 0.001, $P_{H2O}$ = 3.1 kPa, bal He

[b] $x_{O2}$ = 0.003

[c] $x_{O2}$ = 0.005

[d] Selectivity and product yield are C-weighted based on number of moles of CH$_4$ incorporated. (e.g., 1 C/Toluene and 2 C/Xylene); xylene was only observed for the last table entry. Selectivities are calculated upon accounting for contribution of benzene oxidation to observed CO$_2$ rate of formation.

FIG. 8D

| | |
|---|---|
| max $r_{obs}$ (mol $kg_{cat}^{-1}$ $s^{-1}$) | $1.30 \cdot 10^{-6}$ |
| $\Delta H_{rxn}$ (kJ $mol^{-1}$) | -300 |
| $E_a$ (kJ $mol^{-1}$) | 100 |
| Fractional conversion | 0.00004 |
| n | 1 |
| $\rho_{bulk}$ (kg $m^{-3}$) (Assumed $\varepsilon \approx 0.4$) | 750 |

CATALYTIC COMPOSITIONS FOR THE OXIDATION OF SUBSTRATES

RELATED APPLICATIONS

This application claims priority to U.S. Provisional Patent Application Ser. No. 63/002,415, filed Mar. 31, 2020, entitled "Direct Aromatic Alkylation Using Methane Over Copper-Zeolite Systems," and U.S. Provisional Patent Application Ser. No. 63/029,751, filed May 26, 2020, entitled "Catalytic Compositions for the Oxidation of Substrates," both of which are incorporated herein by reference in their entireties for all purposes.

TECHNICAL FIELD

Catalytic compositions and sequential catalytic methods are generally described.

BACKGROUND

The selective oxidation of methane ($CH_4$) to useful products is a significant challenge in catalysis due to a selectivity-conversion limit stemming from the relative ease of continued oxidation of partially oxidized $CH_4$-derived products. This selectivity-conversion limit, combined with the global abundance of natural gas reserves, makes selective $CH_4$ oxidation at mild conditions and small scales an attractive alternative to current large-scale two-step industrial processes. The selective activation of $CH_4$ can be obtained at mild conditions, but $CH_4$ conversion is limited (e.g., to ~0.01%). Selectivity is expected to decrease quickly with increasing $CH_4$ conversion. Therefore, improved compositions and methods related to the oxidation of alkanes (e.g., $CH_4$) are necessary.

SUMMARY

Catalytic compositions and methods are provided, some of which relate to the oxidation of an alkane. The subject matter of the present invention involves, in some cases, interrelated products, alternative solutions to a particular problem, and/or plurality of different uses of one or more systems and/or articles.

According to certain embodiments, a composition is described, the composition comprising a first catalyst comprising a Cu-modified zeolite, and a second catalyst capable of a coupling reaction between (a) an intermediate resulting from a reaction of a reactant at the first catalyst, and (b) a co-reagent, wherein a rate of diffusion of the co-reagent within the cages and/or pores of the first catalyst is lower than a rate of diffusion of the intermediate within the cages and/or pores of the first catalyst.

In certain embodiments, a composition is described, the composition comprising a first catalyst comprising a Cu-modified zeolite, and a second catalyst capable of a coupling reaction, wherein the coupling reaction is alkylation and/or etherification.

According to some embodiments, a method is described, the method comprising exposing a reactant to a first catalyst comprising a Cu-modified zeolite, thereby oxidizing the reactant to provide an intermediate, and exposing the intermediate and a co-reagent to a second catalyst, thereby reacting the co-reagent with the intermediate to provide a product.

In some embodiments, a composition is described, the composition comprising a first catalyst comprising a Cu-modified zeolite, and a second catalyst capable of a coupling reaction between (a) an intermediate resulting from a reaction of a reactant at the first catalyst, and (b) a co-reagent, wherein a rate of diffusion of the co-reagent relative to the first catalyst is lower than a rate of diffusion of the intermediate relative to the first catalyst.

According to certain embodiments, a composition is described, the composition comprising a first catalyst comprising a Cu-modified zeolite, and a second catalyst capable of a coupling reaction between (a) an intermediate resulting from a reaction of a reactant at the first catalyst, and (b) a co-reagent, wherein a rate of diffusion of the co-reagent relative to the first catalyst is lower than a rate of diffusion of the co-reagent relative to the second catalyst.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale unless otherwise indicated. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

In the figures:

FIG. 8D shows, according to some embodiments, the observed $CH_4$ conversion, selectivity, and product yield for tandem oxidation and alkylation over Cu-CHA/H-MFI;

DETAILED DESCRIPTION

Figure 1:
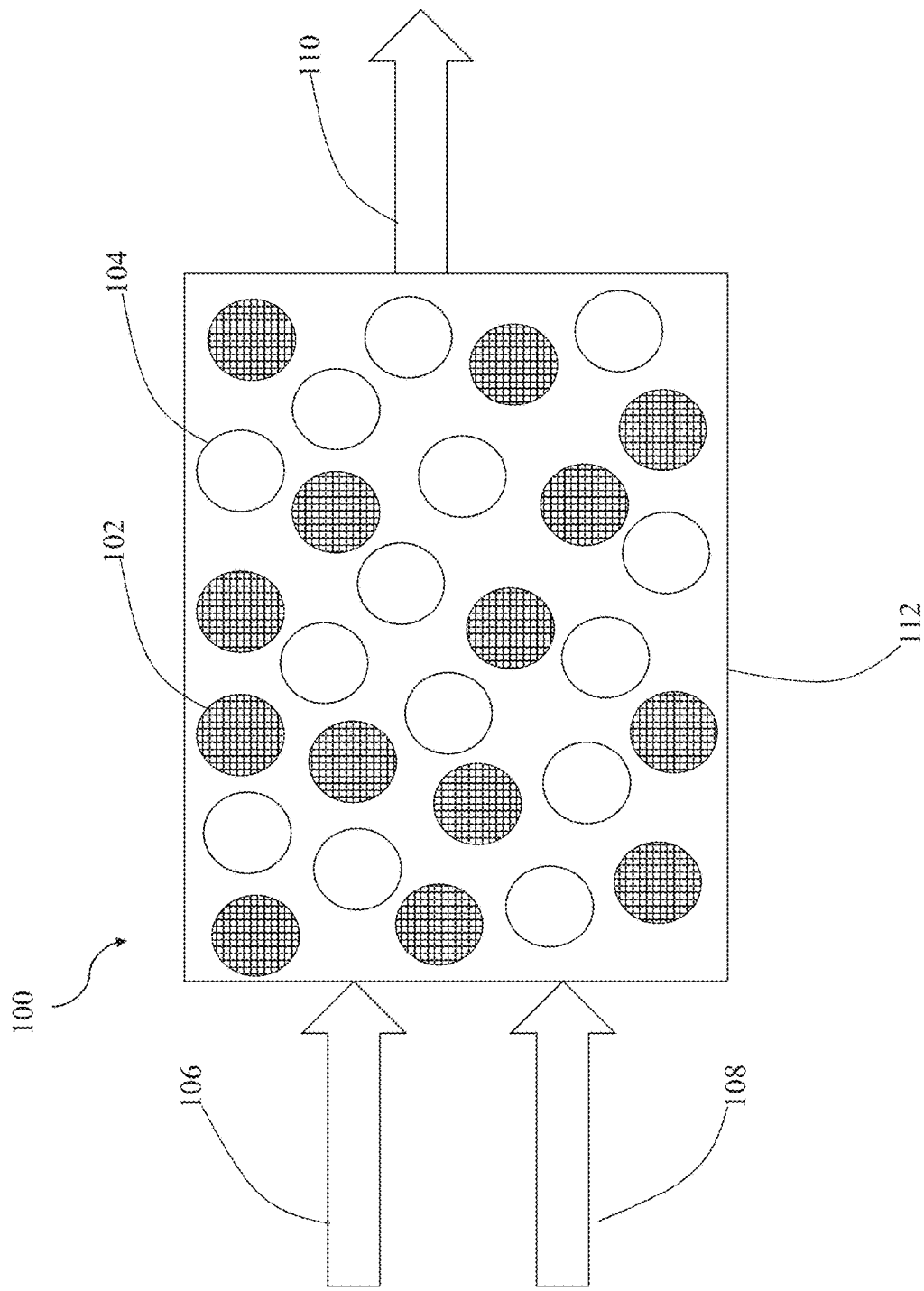
FIG. 1 shows, according to certain embodiments, a schematic diagram of a catalytic composition for oxidizing a reactant.

Catalytic compositions and methods are generally described. In one aspect, a catalytic composition comprises a first catalyst and a second catalyst. The first catalyst may be capable of catalytically oxidizing a reactant to provide an intermediate, while the second catalyst may be capable of a coupling reaction between the intermediate and a co-reagent in a manner in which relative exposure of the co-reagent to the first and second catalysts is controlled. The coupling reaction may, in some embodiments, be an alkylation or an etherification reaction between the intermediate and the co-reagent. For example, in certain embodiments, the first catalyst catalytically oxidizes an alkane (e.g., methane) to an intermediate (e.g., methanol), and the second catalyst couples the reaction between the intermediate and a co-reagent (e.g., benzene) to provide a product (e.g., toluene).

Methane monooxygenases (MMOs) are selective for methane ($CH_4$) activation as a result of a gating mechanism that limits contact of methanol ($CH_3OH$) with the metal (e.g., Cu) active site(s) in order to avoid over-oxidation of methanol to, for example, carbon dioxide ($CO_2$). The gating mechanism employed by MMOs has not been reproduced using conventional synthetic catalysts due to their relatively rigid nature. Furthermore, conventional synthetic methane oxidation systems operate stoichiometrically as opposed to catalytically. Described herein, however, are compositions and methods for chemical scavenging upon the activation of a reactant as a means of mimicking the gating system in MMOs.

In some embodiments, for example, the second catalyst, such as a solid acid catalyst, chemically scavenges the intermediate, such as methanol, which is a product of the catalytic reaction of the reactant at the first catalyst. The second catalyst may be configured to catalytically couple the chemically scavenged intermediate with a co-reagent, such as benzene, thereby providing a product, such as toluene. The rate of diffusion of the co-reagent relative to the first catalyst (e.g., within one or more cages and/or pores of the first catalyst) is lower than the rate of diffusion of the intermediate relative to the first catalyst (e.g., within the one or more cages and/or pores of the first catalyst). A composition comprising the first and second catalysts in such a configuration functions to exclude the co-reagent from entering the cages and/or pores of the first catalyst, thereby mitigating over-oxidation events at one or more active sties of the first catalyst and facilitating the coupling reaction between the scavenged intermediate and the co-reagent by the second catalyst.

While specific examples of catalysts, reactants, intermediates, etc. are used immediately above, those of ordinary skill in the art will recognize the applicability of the invention to many substrates, intermediates, reactants, co-reagents, etc. as will be described more fully further below.

In some embodiments, the tandem catalyst composition functions due to the following factors: (i) the second catalyst does not inhibit oxidation of the reactant (e.g., $CH_4$) by the first catalyst; (ii) the second catalyst and the product (e.g., toluene) are more resistant than the intermediate (e.g., $CH_3OH$) to undesirable over-oxidation (e.g., to $CO_2$); (iii) the rate of the reaction (e.g., the alkylation reaction) between the intermediate (e.g., $CH_3OH$) and the co-reagent (e.g., benzene) is not rate-limiting; and (iv) the distance that the intermediate (e.g., $CH_3OH$) diffuses (e.g., from the first catalyst to the second catalyst) is minimized to limit opportunities for undesirable over-oxidation of the intermediate (e.g., $CH_3OH$) by the first catalyst.

A non-limiting schematic diagram representing a catalytic composition for oxidizing a reactant is shown in FIG. 1. As shown in FIG. 1, composition 100 comprises first catalyst 102 and second catalyst 104. In some embodiments, first catalyst 102 is exposed to stream 106 comprising a reactant. As a result of exposing first catalyst 102 to stream 106 comprising the reactant, the reactant is catalytically oxidized to an intermediate. Second catalyst 104, in some embodiments, is exposed to the intermediate and stream 108 comprising a co-reagent. As a result of exposing second catalyst 104 to the intermediate and stream 108 comprising the co-reagent, the intermediate and the co-reagent are coupled to form stream 110 comprising a product.

Exposing Reactant to First Catalyst

Figure 2:
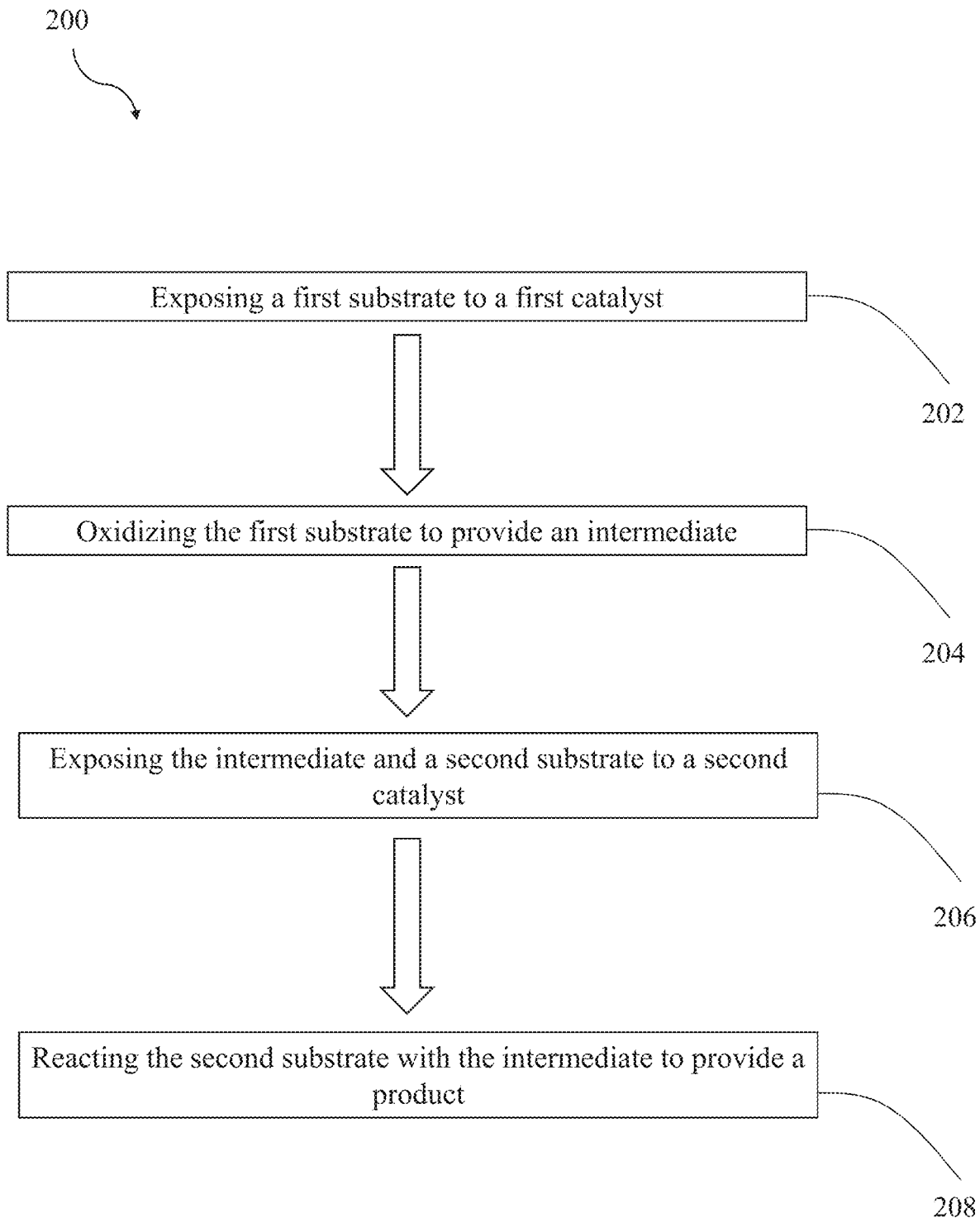
FIG. 2 shows, according to certain embodiments, a flow diagram of a method of oxidizing a reactant to provide an intermediate and coupling the intermediate with a co-reagent.

In certain embodiments, methods of oxidizing a reactant are described. FIG. 2 shows, according to certain embodiments, a flow diagram of a method of oxidizing a reactant to provide an intermediate and coupling the intermediate with a co-reagent. As shown in FIG. 2, method 200 comprises step 202 wherein a reactant (e.g., methane) is exposed to a first catalyst (e.g., a Cu-modified catalyst). The reactant may be exposed to the first catalyst in the gaseous state, in some embodiments. According to certain embodiments, and as shown in step 204, the reactant is oxidized as a result of exposing the reactant to the first catalyst, thereby providing an intermediate (e.g., methanol). In certain embodiments, the intermediate is produced (e.g., from oxidation of the reactant by the first catalyst) in a continuous and/or catalytic process.

As used herein, the phrase "catalytic process" is given its ordinary meaning in the art and generally refers to a continuous process wherein, on average, more than one molecule of product is produced per a single active site of the catalyst. A catalytic process does not include the regeneration of the catalyst through a separate regeneration process. The phrase "stoichiometric process" is given its ordinary meaning in the art as used herein and generally refers to a process in which only one molecule of product is produced per a single active site, wherein the active site is inactive following formation of the molecule of product. Thus, in contrast to a catalytic process, in order to produce more than one molecule of product per a single active site during a stoichiometric process, the active site must be regenerated through a separate regeneration process. In some embodiments, in which the precise number of active sites has not been fully determined, but has been limited to a particular class, such as moles of a particular metal (for example, copper), the total number of moles of that metal serve as a ceiling to the number of possible active sites. According to such embodiments, a process is catalytic where the moles of product generated exceed the moles of that metal (e.g., copper), without requiring a separate regeneration process.

The production of an intermediate (e.g., methanol) from a reactant (e.g., methane) is further described in U.S. Pat. No. 10,099,979, entitled "Catalytic Methods for the Production of an Alcohol from an Alkane", which is incorporated herein by reference in its entirety for all purposes.

Reactant

As noted above, based on the disclosure herein relating to the provision of catalysts with general properties related to advantageous reactions involving reactants, intermediates, and co-reagents, those of ordinary skill in the art based on this disclosure will readily be able to select suitable catalysts and reagents from a wide range of species, and will be able to identify, without undue experimentation, which catalysts and reagents can be used in connection with the invention.

The reactant may be any of a variety of suitable substrates. According to certain embodiments, the reactant comprises an alkane represented by the for $C_nH_{2n+2}$. In some embodiments, for example, the reactant comprises methane, ethane, propane, or butane. Mixtures of reactant are also possible (e.g., the reactant comprises methane and ethane, for example). According to some embodiments, the reactant may be optionally substituted. For example, in certain embodiments, the reactant may be represented by the general formula $R^1CH_3$, wherein $R^1$ is hydrogen, an unsubstituted alkyl group, or an optionally substituted alkyl group.

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, hepta), octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., C1-C12 for straight chain, C3-C12 for branched chain), 6 or fewer, or 4 or fewer. Thus, as used herein, the term "alkyl" includes straight, branched and cyclic alkyl groups.

First Catalyst

The first catalyst may be selected from any of a variety of suitable catalysts. In some embodiments, the first catalyst comprises a zeolite. As used herein, the term "zeolite" generally refers to a crystalline porous material having a framework of oxides comprising silicon and, optionally, aluminum and/or one or more additional elements (e.g., boron, gallium, and/or phosphorous). According to some embodiments, the zeolite comprises a silicate framework, an aluminosilicate framework, a silicoaluminophosphate framework, a borosilicate framework, a gallosilicate framework, or a zincosilicate framework. In certain embodiments, the zeolite comprises a framework comprising a trivalent metal.

Examples of zeolites that may be used as a framework of the first catalyst include, but are not limited to, AEI, AFX, mazzite (MAZ), mordenite (MOR), ferrierite, (FER), beta (BEA), chabazite (CHA), and mobil composition of matter (MCM). Other commercially or non-commercially available zeolites may also be implemented. In some embodiments, mixtures of zeolites may be implemented as the first catalyst.

According to some embodiments, a framework of the first catalyst may be charged (e.g., negatively charged). For example, in certain embodiments, the framework of the zeolite creates a charge imbalance that is compensated by counter cations. The framework of the first catalyst (e.g., zeolite) is generally anionic, and the counter cations that balance the charge of the anionic framework may be associated with the framework (e.g., on the surface of the first catalyst, within one or more pores of the framework). In some embodiments, the zeolite may be modified such that at least a portion of the counter cations associated with the framework are exchanged (e.g., with other counter cations), as desired for a particular application. In some embodiments, for example, the zeolite may be modified by at least partially exchanging one or more counter cations with a transition metal, thereby providing a modified zeolite. According to some embodiments, for example, the zeolite may be modified with Cu and/or Fe. Any of the above listed zeolite frameworks may be modified with a transition metal (e.g., Cu). The transition metal, in some embodiments, may be present within one or more cages and/or pores of the first catalyst. In certain non-Limiting embodiments, for example, the first catalyst comprises Cu-modified SSL-13.

The first catalyst may comprise any of a variety of suitable amounts of the transition metal used to modify the first catalyst. In certain embodiments, for example, the first catalyst comprises the transition metal used to modify the first catalyst in an amount greater than 0.1 wt. %, greater than 0.5 wt. %, greater than 1 wt. %, greater than 1.5 wt. %, greater than 2 wt. %, greater than 2.5 wt. %, greater than 3 wt. %, greater than 3.5 wt. %, greater than 4 wt. %, or greater than 4.5 wt. % based on the total weight of the first catalyst. In some embodiments, the first catalyst comprises the transition metal used to modify the first catalyst in an amount less than or equal to 5 wt. %, less than or equal to 4.5 wt. %, less than or equal to 4 wt. %, less than or equal to 3.5 wt. %, less than or equal to 3 wt. %, less than or equal to 2.5 wt. %, less than or equal to 2 wt. %, less than or equal to 1.5 wt. %, less than or equal to 1 wt. %, or less than or equal to 0.5 wt. %. % based on the total weight of the first catalyst. The amount of transition metal used to modify the first catalyst may be determined by elemental analysis techniques, such as inductively coupled plasma atomic emission spectroscopy (ICP-AES) and/or inductively coupled plasma mass spectrometry (ICP-MS).

According to certain embodiments, it may be beneficial to remove and/or exchange one or more metal sites on the surface of the first catalyst in order to inhibit over-oxidation events from occurring at the surface of the first catalyst. In some embodiments, for example, the surface of the first catalyst may be modified to reduce surface acidity and/or remove one or more metals in order to mitigate the reactant (e.g., $CH_4$) and/or the co-reagent (e.g., benzene) from over-oxidizing as the reactant and/or the co-reagent are exposed to one more compositions described herein. In some embodiments, for example, the surface of the first catalyst may be modified by dealumination of surface aluminum. Dealumination, in some embodiments, may be achieved by dealuminating the first catalyst with an organic-structure-directing agent used during the synthesis of the first catalyst, which may be associated with the first catalyst after synthesis. In certain embodiments, the surface of the first catalyst may be modified by silylation.

According to certain embodiments, the first catalyst comprises a zeolite (e.g., a Cu-modified zeolite) comprising one or more cages and/or pores. As explained in further detail below, it may be advantageous, in some embodiments, to employ a zeolite as the first catalyst with one or more cages and/or pores that are large enough to allow the reactant (e.g., methane) to diffuse into the one or more cages and/or pores of the zeolite, but small enough to exclude the co-reagent from diffusing into the one or more cages and/or pores of the zeolite. As a result, the co-reagent does not inhibit the selective oxidation of the reactant by the first catalyst. Furthermore, the co-reagent is not subject to over-oxidation by one or more active sites of the first catalyst since the co-regent is too large to diffuse into one or more the cages and/or pores of the first catalyst. In some embodiments, for example, the first catalyst is a zeolite comprising 8-member ring pores.

In certain embodiments, wherein the first catalyst is a zeolite, the zeolite may have any of a variety of suitable cage and/or pore sizes. In some embodiments, for example, the zeolite (e.g., Cu-modified zeolite) comprises cage and/or pores with an average characteristic dimension, such as an average diameter of the pore and/or cage.

In certain embodiments, the average characteristic dimension (e.g., average diameter) of the cages and/or pores of the zeolite is less than or equal to 5 angstroms, less than or equal to 4.5 angstroms, less than or equal to 4 angstroms, less than or equal to 3.5 angstroms, less than or equal to 3 angstroms, or less than or equal to 2.5 angstroms. In certain embodiments, the zeolite (e.g., Cu-modified zeolite) comprises cages and/or pores with an average characteristic dimension (e.g., average diameter) of greater than or equal to 2 angstroms, greater than or equal to 2.5 angstroms, greater than or equal to 3 angstroms, greater than or equal to 3.5 angstroms, greater than or equal to 4 angstroms, or greater than or equal to 4.5 angstroms. Combinations of the above recited ranges are also possible (e.g., the zeolite comprises cages and/or pores with an average characteristic dimension of less than or equal to 5 angstroms and greater than or equal to 2 angstroms, the zeolite comprises cages and/or pores with an average characteristic dimension of less than or equal to 3.5 angstroms and less than or equal to 4.5 angstroms). Other ranges are also possible. Methods of determining the average diameter of the zeolite cages and/or pores include powder X-ray diffraction and scanning electron microscopy (SEM).

Oxidizing Agent and Solvent.

According to certain embodiments, the reactant is exposed to the first catalyst in the presence of an oxidizing agent and a solvent. In some embodiments, one of or both the oxidizing agent and the solvent may be in the gaseous state when exposed to the first catalyst. In certain embodiments, one or both of the oxidizing agent and the solvent may be exposed to the first catalyst concurrently with the reactant. Referring to FIG. 1, for example, stream 106 comprising the reactant may also comprise the oxidizing agent and/or the solvent. In some such embodiments, first catalyst 102 may be exposed to the reactant, the oxidizing agent, and the solvent via stream 106.

As used herein, the term "oxidizing agent" is given its ordinary meaning in the art and generally refers to a chemical species that has the ability to oxidize or increase the oxidation state of another chemical species. In the processes described herein, the oxidizing agent generally serves as an oxidizing source for the reaction of oxidizing the reactant (e.g., alkane) to the intermediate. Without wishing to be bound by theory, for example, the oxidizing agent may form a reactive species at the active site of the first catalyst (e.g., a copper-oxo site), thereby resulting in a catalytically active species that may oxidize the reactant to the intermediate. In some embodiments, prior to the exposing the reactant to the first catalyst, the first catalyst may be activated by exposing the catalyst to the oxidizing agent. According to some non-limiting embodiments, the oxidizing agent comprises dioxygen ($O_2$). Other non-limiting examples of an oxidizing agent include ozone ($O_3$), nitric oxide, nitrous oxide, and hydrogen peroxide. Alternative or additional oxidizing agents or a combination of oxidizing agents may be used, in some embodiments.

It may be advantageous, in certain embodiments, to utilize the solvent in order to diffuse the intermediate from the first catalyst to the second catalyst, resulting in chemical scavenging of the intermediate by the second catalyst, as explained herein in greater detail. In some non-limiting embodiments, the solvent comprises water ($H_2O$). In certain embodiments, the solvent comprises an alcohol, such as ethanol. Alternative or additional solvents or a combination of solvents may be used, in some embodiments.

Without wishing to be bound by theory, the oxidation of the reactant to the intermediate may occur at one or more active sites within the first catalyst. In some embodiments, for example, the oxidation of the reactant to the intermediate may occur at one or more active sites (e.g., active metal sites) within the first catalyst (e.g., Cu-modified zeolite). The one or more active sites within the first catalyst may be tolerant to both the oxidizing agent (e.g., $O_2$) and the solvent (e.g., $H_2O$), in some embodiments, resulting in the continuous operation of the active sites for performing the oxidation of the reactant without having to be separately reactivated and/or regenerated, therefore producing more moles of the intermediate than the total number of moles of the active site present in the first catalyst. As compared to conventional methods, the continuous catalytic operation of the first catalyst as described herein is in contrast with a stoichiometric process for oxidizing reactants (e.g., alkanes), which results in one or less than one molecule of oxidized product per active site, thereby requiring reactivation and/or regeneration of the active sites.

Intermediate

In some embodiments, the intermediate comprises an activated and/or oxidized reactant. For example, in certain embodiments, wherein the reactant is an alkane, the intermediate comprises an oxidized alkane. In some embodiments, the intermediate is a saturated alcohol. For example, in some embodiments, the intermediate may be represented by the general formula $C_nH_{2n+1}OH$. The intermediate may, in some embodiments, be thermodynamically stable. According to certain embodiments, the intermediate comprises methanol, ethanol, propanol, or butanol, any of which may be optionally substituted. In certain embodiments, mixtures of intermediates are also possible (e.g., the intermediate comprises methanol and ethanol, for example).

The intermediate may be formed with a high intermediate selectivity. As used herein, the term "intermediate selectivity" is defined as:

$$S_i = \frac{C_i F_i}{\sum_{i=1}^N C_i F_i}$$

where $S_i$ is the selectivity of intermediate i on a C-atom basis, $C_i$ is the number of carbon atoms incorporated from the reactant into intermediate i, $F_i$ is the molar flow rate of intermediate i, and $\Sigma C_i F_i$ is the total molar flow rate of carbon of all products produced by the oxidizing reaction. Without wishing to be bound by theory, other products produced by the oxidizing reaction may include carbon monoxide (CO) and/or carbon dioxide ($CO_2$).

In some embodiments, the intermediate is formed with an intermediate selectivity greater than or equal to 70%, greater than or equal to 75%, greater than or equal to 80%, greater than or equal to 85%, greater than or equal to 90%, or greater than or equal to 95%. In certain embodiments, the intermediate is formed with an intermediate selectivity less than or equal to 99%, less than or equal to 95%, less than or equal to 90%, less than or equal to 85%, less than or equal to 80%, or less than or equal to 75%. Combinations of the above recited ranges are also possible (e.g., the intermediate is formed with an intermediate selectivity greater than or equal to 70% and less than or equal to 99%, the intermediate is formed with an intermediate selectivity greater than or equal to 80% and less than or equal to 85%). Other ranges are also possible.

Exposing Intermediate and Co-Reagent to Second Catalyst

Referring to FIG. 2, according to some embodiments, method 200 comprises step 206 wherein the intermediate (e.g., methanol) and a co-reagent (e.g., benzene) are exposed to a second catalyst (e.g., a proton-form zeolite). In some embodiments, one or both of the intermediate and the co-reagent may be in the gaseous state when exposed to the second catalyst. In certain embodiments, and as shown in step 208, the intermediate reacts with the co-reagent as a result of exposing the intermediate and the co-reagent to the second catalyst, thereby providing a product (e.g., toluene). In certain embodiments, the product is produced (e.g., from a coupling reaction between the intermediate and the co-reagent) in a continuous and/or catalytic process.

Co-Reagent

The co-reagent may be any of a variety of suitable substrates. In some embodiments, the co-reagent comprises an aromatic, an alcohol, a cyclic compound, and/or an alkene, any of which may be optionally substituted. In some embodiments, non-limiting embodiments of co-reagents include, but are not limited to, benzene, naphthalene, anthracene, toluene, ethylbenzene, phenol, aniline, acetophenone, benzaldehyde, benzoic acid, benzonitrile, xylene, mesitylene, durene, styrene, biphenyl, benzyl alcohol, cyclohexene, cyclohexanol, cyclohexanone, hexene, and butene isobutylene). Mixtures of co-reagents are also possible (e.g., the co-reagent comprises benzene and toluene, for example).

In certain embodiments, it may be beneficial to employ a co-reagent that has a lower rate of diffusion relative to the first catalyst than a rate of diffusion of the intermediate relative to the first catalyst. Utilizing a co-reagent that has a lower rate of diffusion relative to the first catalyst than a rate of diffusion of the intermediate relative to the first catalyst may advantageously inhibit the over-oxidation of the co-reagent at one or more active sites of the first catalyst, therefore facilitating the coupling reaction between the intermediate and the co-reagent at the second catalyst, which is explained in greater detail below. As used herein, "rate of diffusion" is given its ordinary meaning in the art and refers to the change in the concentration of a diffusing species over time. According to some embodiments, for example, the rate of diffusion of a species relative to the first catalyst may, for example, encompass the rate of diffusion of a species to a surface of the catalyst, the rate of diffusion of a species to one or more active sites of the first catalyst, and/or the rate of diffusion of a species within one or more cages and/or pores of the first catalyst. In some embodiments, for example, the rate of diffusion of the co-reagent relative to the first catalyst is no more than 60%, no more than 50%, no more than 40%, no more than 30%, no more than 20%, no more than 10%, no more than 5%, or no more than 1% the rate diffusion of the intermediate relative to the first catalyst.

In some embodiments, the co-reagent has a lower rate of diffusion within the cages and/or pores of the first catalyst than a rate of diffusion of the intermediate within the cages and/or pores of the first catalyst. In some embodiments, for example, the rate of diffusion of the co-reagent within the cages and/or pores of the first catalyst is no more than 60%, no more than 50%, no more than 40%, no more than 30%, no more than 20%, no more than 10%, no more than 5%, or no more than 1% the rate diffusion of the intermediate within the cages and/or pores of the first catalyst.

In certain embodiments, the co-reagent has a lower rate of diffusion relative to the first catalyst than a rate of the diffusion of the co-reagent relative to the second catalyst. Advantageously, utilizing a co-reagent that has a lower rate of diffusion relative to the first catalyst than a rate of diffusion of the co-reagent relative to the second catalyst may promote the co-reagent to diffuse to one or more active sites of the second catalyst, therefore facilitating the coupling reaction between the co-reagent and the intermediate provided by the oxidation of the reactant at the first catalyst.

According to certain embodiments, and as mentioned above, the co-reagent may be chosen by one of ordinary skill in the art such that diffusion of the co-reagent into the cages and/or pores of the first catalyst (e.g., the Cu-modified zeolite) is inhibited or prevented. For example, in some embodiments, a size of the co-reagent may be too large to diffuse into the cages and/or pores of the first catalyst (e.g., the Cu-modified zeolite). In certain embodiments, the co-reagent has an average characteristic dimension that is larger than the average characteristic dimension (e.g., average diameter) of the cages and/or pores of the first catalyst. In some embodiments, the average characteristic dimension of the co-reagent may be a kinetic diameter, an average length of the molecule, an average diameter of the molecule, and/or the like.

Although conventions for measuring the size of the co-reagent and ability of the co-reagent to access the first catalyst, for example, via passage through pores and/or cage openings (or inhibition thereof) is discussed, specific conventions for measurement are less important than the concept presented in this disclosure that inhibition or prevention of access to the first catalyst by the co-reagent is desired, in some embodiments. With the benefit of that concept, those of ordinary skill in the art will readily be able to measure co-reagents and design catalyst structures accordingly.

Control of inhibition of access to the first catalyst by the co-reagent is described herein via selection of a pore or cage structure of the catalyst. In another set of embodiments, an auxiliary filter or the like can be positioned between the source of the co-reagent and the first catalyst. For example, the first catalyst might not be porous or have a caged structure, but can be at least partially covered by a filter with, for example, the requisite porosity. In another set of embodiments, the first catalyst is porous, but an auxiliary filter is also provided. Based upon the conceptual discussion herein, those of ordinary skill in the art can readily select appropriate filters, for example, molecular sieves, metal-organic frameworks, other filters of appropriate porosity, etc. In this arrangement, all that is needed is that the filter and/or the cage structure or porosity of the catalyst, alone or together, inhibits or prevents contact of the first catalyst by the co-reagent as desired.

In some embodiments, the average characteristic dimension (e.g., kinetic diameter) of the co-reagent is greater than or equal to 4.5 angstroms, greater than or equal to 5 angstroms, greater than or equal to 5.5 angstroms, greater than or equal to 6 angstroms, or greater than or equal to 6.5 angstroms. In some embodiments, the average characteristic dimension (e.g., kinetic dimeter) of the co-reagent is less than or equal to 7 angstroms, less than or equal to 6.5 angstroms, less than or equal to 6 angstroms, less than or equal to 5.5 angstroms, or less than or equal to 5 angstroms. Combinations of the above recited ranges are also possible (e.g., the average characteristic dimension of the co-reagent is greater than or equal to 4.5 angstroms and less than or equal to 7 angstroms, the average characteristic dimension of the co-reagent is less than or equal to 6 angstroms and greater than or equal to 5.5 angstroms). Other ranges are also possible.

Second Catalyst

The second catalyst may be selected from any of a variety of suitable catalysts. According to certain embodiments, the second catalyst is capable of a coupling reaction. The coupling reaction, in certain embodiments, is a reaction between the intermediate resulting from the reaction of the reactant at the first catalyst, and the co-reagent. In some embodiments, for example, the second catalyst is capable of coupling the co-reagent and the intermediate. Some non-limiting examples of coupling reactions include, for example, alkylation and/or etherification.

In some embodiments, the second catalyst is a solid acid catalyst. For example, in certain embodiments, the solid acid catalyst may comprise one or more Bronsted acid sites and display Bronsted acid characteristics. Without wishing to be bound by theory, in some embodiments, the coupling reaction occurs at the one more Bronsted acid sites within the second (e.g., solid acid) catalyst. In certain embodiments, the Bronsted acid sites comprise a plurality of catalytically active acidic hydroxyls, for example. The second catalyst may comprise, in some embodiments, a zeolite, a metal oxide, a metal-organic-framework (MOF), a heteropoly acid, a polyoxometallate, sulfated zirconia, hypophosphorous acid, aluminophosphate (AlPO), silicoaluminophosphate (SAPO), and/or combinations thereof.

The metal oxide may comprise, in some embodiments, alumina, silica, molybdenum oxide, tungsten oxide and/or the like. In some aspects, the metal oxide may be treated and/or untreated. In certain embodiments, the metal oxide may be associated with a support, such as an aluminosilicate support.

In certain embodiments, the second catalyst comprises a zeolite (e.g., a proton-form zeolite). According to some embodiments, the zeolite comprises a silicate framework, an aluminosilicate framework, a silicoaluminophosphate framework, a borosilicate framework, a gallosilicate framework, or a zincosilicate framework. According to certain embodiments, the zeolite comprises framework comprising a trivalent metal.

Examples of zeolites that may be used as a framework of the second catalyst include, but are not limited to, ZSM-5, ZSM-22, SSZ-33, and/or beta (BEA). According to certain non-limiting embodiments, for example, the second catalyst comprises ZSM-5. Other commercially or non-commercially available zeolites may also be implemented.

According to certain embodiments, one or more metal sites on the surface of the second catalyst may be exchanged and/or removed to inhibit over-oxidation events from occurring at the surface of the second catalyst. In some embodiments, for example, the surface of the second catalyst may be modified to reduce surface acidity and/or remove one or more metals in order to mitigate the reactant (e.g., $CH_4$) and/or the co-reagent (e.g., benzene) from over-oxidizing as the reactant and/or the co-reagent are exposed to one more compositions described herein. In some embodiments, for example, the surface of the second catalyst be modified by dealumination of surface aluminum. Dealumination, in some embodiments, may be achieved by dealuminating the second catalyst. In certain embodiments, the surface of the second catalyst may be modified by silylation.

Product

In certain embodiments, the product comprises a reaction product (e.g., coupled reaction product) between any of the aforementioned intermediates and any of the aforementioned co-reagents. In certain embodiments, for example, the product comprises an alkylated product resulting from the coupling reaction between the intermediate (e.g., methanol)

and the co-reagent (e.g., benzene). In some embodiments, for example, the product comprises toluene, xylene (e.g., ortho-, meta-, and/or para-xylene), or anisole. As would be understood by a person of ordinary skill in the art, other products are possible depending on the choice of intermediate and co-reagent, as explained in further detail above. Mixtures of products are also possible, in some embodiments (e.g., the product comprises toluene and xylene).

The product may be formed with a high product selectivity. As used herein, the term "product selectivity" is defined as:

$$S_i = \frac{C_i F_i}{\sum_{i=1}^{N} C_i F_i}$$

where $S_i$ is the selectivity of product i on a C-atom basis, $C_i$ is the number of carbon atoms incorporated from the reactant into product i, $F_i$ is the molar flow rate of product i, and $\Sigma C_i F_i$ is the total molar flow rate of carbon of all products. Without wishing to be bound by theory, other products produced may include carbon monoxide (CO) and/or carbon dioxide ($CO_2$).

In some embodiments, the product is formed with a product selectivity greater than or equal to 70%, greater than or equal to 75%, greater than or equal to 80%, greater than or equal to 85%, greater than or equal to 90%, or greater than or equal to 95%. In certain embodiments, the product is formed with a product selectivity less than or equal to 99%, less than or equal to 95%, less than or equal to 90%, less than or equal to 85%, less than or equal to 80%, or less than or equal to 75%. Combinations of the above recited ranges are also possible (e.g., the product is formed with a product selectivity greater than or equal to 70% and less than or equal to 99%, the product is formed with a product selectivity greater than or equal to 80% and less than or equal to 85%). Other ranges are also possible.

The product may be formed with a high reactant conversion percentage. As used herein, the term "conversion percentage" is defined as:

$$X_R = \frac{\sum_{i=1}^{N} C_i F_i}{F_R}$$

where $X_R$ is the conversion of reactant, $F_i$ is the molar flow rate of product i, $C_i$ is the number of carbon atoms incorporated from the reactant into product i, $\Sigma C_i F_i$ is the total molar flow rate of carbon of all products, and $F_R$ is the initial molar flow rate of reactant.

In certain embodiments, the product is formed with a reactant conversion percentage greater than or equal to 0.1%, greater than or equal to 0.2%, greater than or equal to 0.3%, greater than or equal to 0.4%, greater than or equal to 0.5%, greater than or equal to 0.6%, greater than or equal to 0.7%, greater than or equal to 0.8%, greater than or equal to 0.9%, or greater than or equal to 1%. In some embodiments, the product is formed with a reactant conversion percentage less than or equal to 1.5%, less than or equal to 1%, less than or equal to 0.9%, less than or equal to 0.8%, less than or equal to 0.7%, less than or equal to 0.6%, less than or equal to 0.5%, less than or equal to 0.4%, less than or equal to 0.3%, or less than or equal to 0.2%. Combinations of the above recited ranges are also possible (e.g., the product is formed with a reactant conversion percentage greater than or equal to 0.1% and less than or equal to 1.5%). Other ranges are also possible.

Reaction Conditions

The ratio (e.g., molar ratio) of the first catalyst and the second catalyst may be any of a variety of suitable ratios. In certain embodiments, for example, the ratio (e.g., weight ratio) of the first catalyst to the second catalyst is greater than or equal to 0.1:1, greater than or equal to 0.2:1, greater than or equal to 0.3:1, greater than or equal to 0.4:1, greater than or equal to 0.5:1, greater than or equal to 1:1, greater than or equal to 2:1, greater than or equal to 3:1, greater than or equal to 4:1, or greater than or equal to 5:1. In some embodiments, the ratio (e.g., weight ratio) of the first catalyst to the second catalyst is less than or equal to 5:1, less than or equal to 4:1, less than or equal to 3:1, less than or equal to 2:1, less than or equal to 1:1, less than or equal to 0.5:1, less than or equal to 0.4:1, less than or equal to 0.3:1, less than or equal to 0.2:1, or less than or equal to 0.1:1. Combinations of the above recited ranges are also possible (e.g., the weight ratio of the first catalyst to the second catalyst is greater than or equal to 0.1:1 and less than or equal to 5:1). Other ranges are also possible.

In certain non-limiting embodiments, it may be advantageous to employ a greater amount of the second catalyst in order to minimize the intermediate diffusion pathway from the first catalyst to the second catalyst. In some embodiments, minimizing the diffusion pathway decreases the number of over-oxidation events of the intermediate caused by the first catalyst. In some such embodiments, the ratio (e.g., weight ratio) of the first catalyst to the second catalyst may be greater than 0.1:1 and less than 1:1.

In some embodiments, the first catalyst and the second catalyst are a mixture. According to certain embodiments, for example, the first catalyst and the second catalyst may be mixed by vortexing the first catalyst and the second catalyst as powders. The mixed powders of the first catalyst and the second catalyst may be pelletized (e.g., after mixing), in some embodiments.

In certain embodiments, the mixture of the first catalyst and the second catalyst (e.g., pelletized mixture) may be placed in an apparatus suitable for carrying out the catalytic reactions. In some embodiments, for example, the first catalyst and the second catalyst may be placed in a reactor (e.g., a catalyst reactor bed). Referring to FIG. 1, for example, first catalyst 102 and second catalyst 104 may be placed in rector 112, in some embodiments. According to certain embodiments, both the first catalyst and the second catalyst are concurrently exposed to the reactant and the co-reagent (e.g., in the gaseous state). For example, referring to FIG. 1, composition 100 may comprise a mixture of first catalyst 102 and second catalyst 104, and said mixture is concurrently exposed to stream 106 comprising a reactant and stream 108 comprising a co-reagent. In some embodiments, stream 106 and/or stream 108 may be introduced to reactor 112 from a single inlet or from multiple inlets, Stream 106 and/or stream 108 may, in some embodiments, be introduced to the reactor continuously, for example, when the reactor is operating in a continuous mode, and a continuous reaction is taking place. According to some embodiments, the reactor may be sealed to an external atmosphere, in which no new matter enters or exits the reactor during operation in a hatch mode.

The step of exposing the reactant to the first catalyst and/or the step of exposing the intermediate and the co-reagent to the second catalyst may occur at any of a variety of temperatures. In some embodiments, one or both of the exposing steps are performed at a temperature greater than or equal to 100° C., greater than or equal to 150° C., greater than or equal to 200° C., greater than or equal to 250° C., greater than or equal to 300° C., greater than or equal to 350° C., greater than or equal to 400° C., or greater than or equal to 450° C. In certain embodiments, one or both of the exposing steps are performed at a temperature less than or equal to 500° C., less than or equal to 450° C., less than or equal to 400° C., less than or equal to 350° C., less than or equal to 300° C., less than or equal to 250° C., less than or equal to 200° C., or less than or equal to 150° C. Combinations of the above recited ranges are also possible (e.g., one or both of the exposing steps are performed at a temperature greater than or equal to 100° C. and less than or equal to 500° C., one or both of the exposing steps are performed at a temperature greater than or equal to 200° C., and less than or equal to 400° C.). Other ranges are also possible.

The step of exposing the reactant to the first catalyst and/or the step of exposing the intermediate and the co-reagent to the second catalyst may occur at any of a variety of pressures. In some embodiments, one or both of the exposing steps are performed at a pressure greater than or equal to 1 bar, greater than or equal to 5 bar, greater than or equal to 10 bar, greater than or equal to 15 bar, greater than or equal to 20 bar, greater than or equal to 25 bar, greater than or equal to 30 bar, or greater than or equal to 35 bar. In certain embodiments, one or both of the exposing steps are performed at a pressure less than or equal to 40 bar, less than or equal to 35 bar, less than or equal to 30 bar, less than or equal to 25 bar, less than or equal to 20 bar, less than or equal to 15 bar, less than or equal to 10 bar, or less than or equal to 5 bar. Combinations of the above recited ranges are also possible (e.g., one or both of the exposing steps are performed at a pressure greater than or equal to 1 bar and less than or equal to 40 bar, one or both of the exposing steps are performed at a pressure greater than or equal to 5 bar and less than or equal to 15 bar).

The following example is intended to illustrate certain embodiments of the present invention, but does not exemplify the full scope of the invention.

Example 1

The following examples describes the oxidation of a reactant by a first catalyst to provide an intermediate, and the coupling reaction of the intermediate with a co-reagent facilitated with a second catalyst.

Figure 10A:
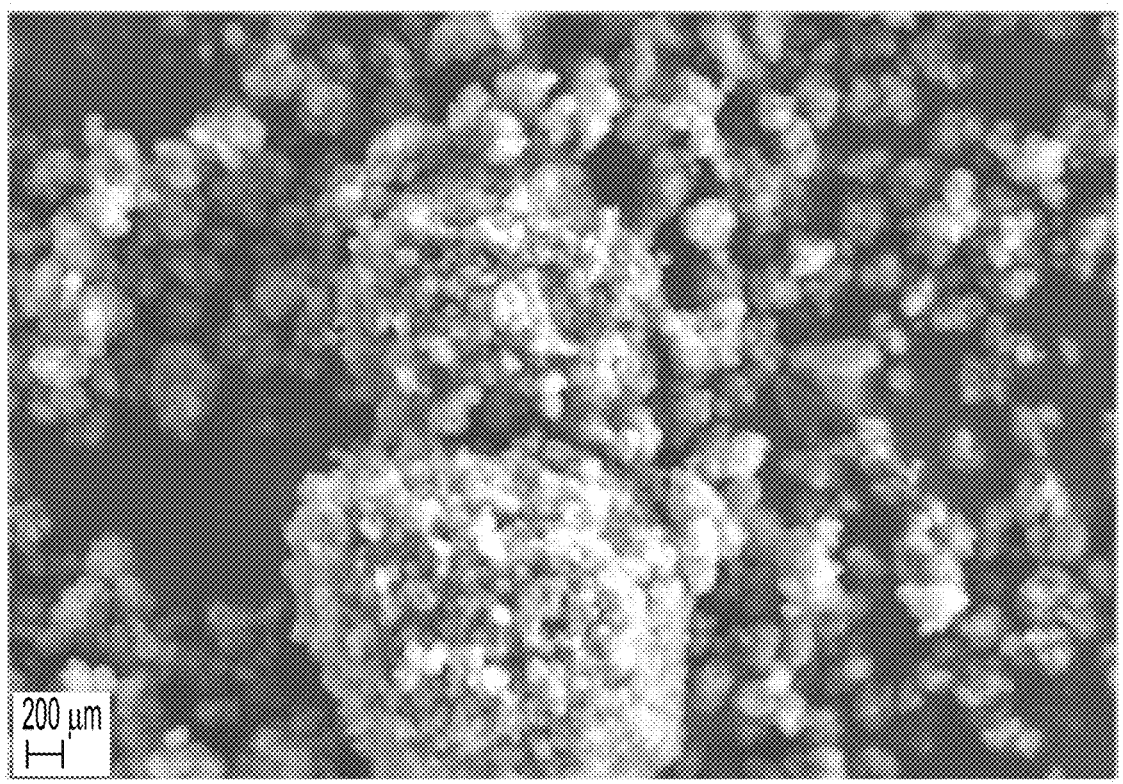
FIG. 10A shows, according to some embodiments, a scanning electron microscopy image of Cu-CHA-1.
Figure 10B:
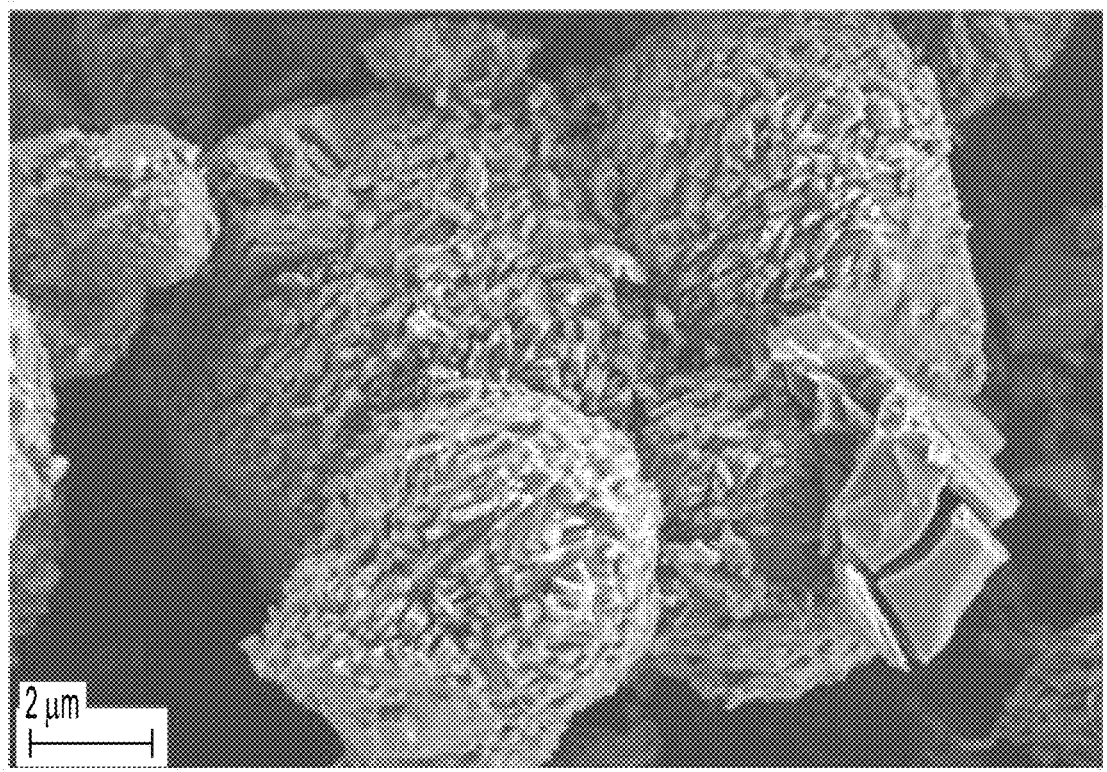
FIG. 10B shows, according to some embodiments, a scanning electron microscopy image of H-MFI-1.
Figure 11B:
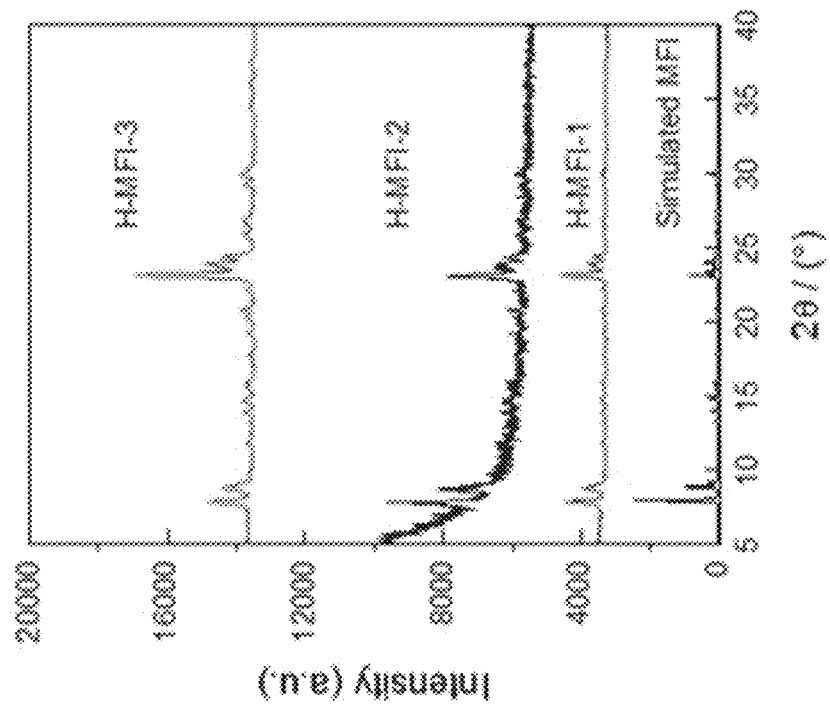
FIG. 11B shows, according to some embodiments, a powder X-ray diffraction pattern of H-MFI-1 and H-MFI-2.
Figure 11A:
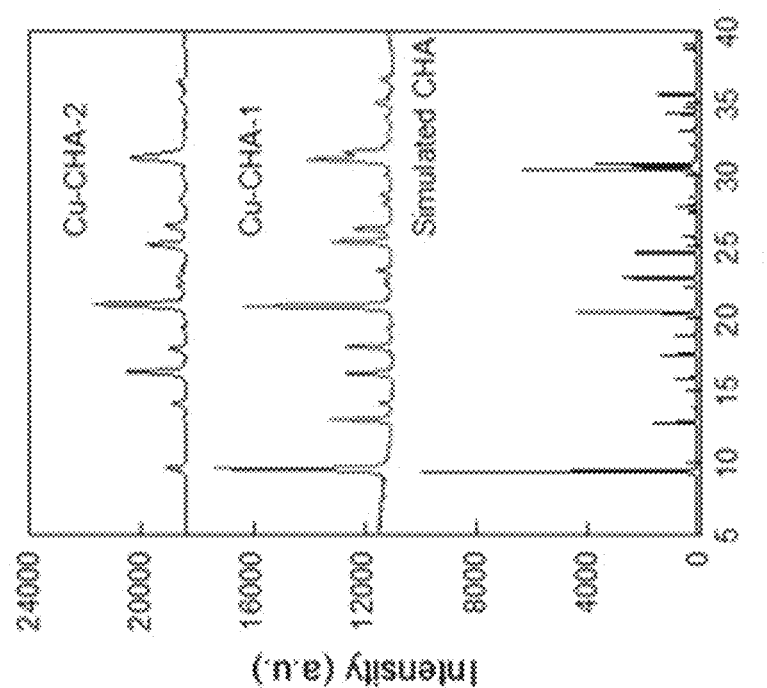
FIG. 11A shows, according to some embodiments, a powder X-ray diffraction pattern of Cu-CHA-1 and Cu-CHA-2.

Cu-SSZ-13 catalysts (denoted Cu-CHA) were synthesized to contain no Na and an abundance of Al to facilitate active site formation, and Cu content was chosen so that Cu/cage <0.3 to avoid the formation of undesirable Cu oxides. H-ZSM-5 (denoted H-MFI) was synthesized to contain no Fe and an abundance of Al, and thereby protons, to enable benzene alkylation. The compositions of some non-limiting catalysts are summarized in Table 1. SEM images Cu-CHA-1 and H-MFI-1 are shown in FIGS. 10A and 10B, respectively. X-ray diffraction patterns of Cu-CHA-1/Cu-CHA-2 and H-MFI-1/H-MFI-2 are shown in FIGS. 11A and 11B, respectively.

TABLE 1

Composition of Cu-CHA and H-MFI catalysts.

| Catalyst | Composition | | Cu Content (wt %) |
|---|---|---|---|
| | Si/Al | Cu/Al | |
| Cu-CHA-1 | 11 | 0.13 | 1.1 |
| Cu-CHA-2 | 13 | 0.13 | 0.9 |
| H-MFI-1 | 19 | — | — |
| H-MFI-2 | 16 | — | — |
| H-MFI-3 | 15 | — | — |

To minimize the number of downstream over oxidation events from $CH_4$ to $CH_3OH$ to $CO_2$, the diffusion path of $CH_3OH$ was minimized by combining Cu-CHA and H-MFI with a larger amount of H-MFI than Cu-CHA (e.g., 1:3 Cu-CHA:H-MFI by weight, denoted Cu-CHA/H-MFI). Cu-CHA and H-MFI were intimately mixed by vortexing the fine powders together prior to pelletizing.

Figure 3A:
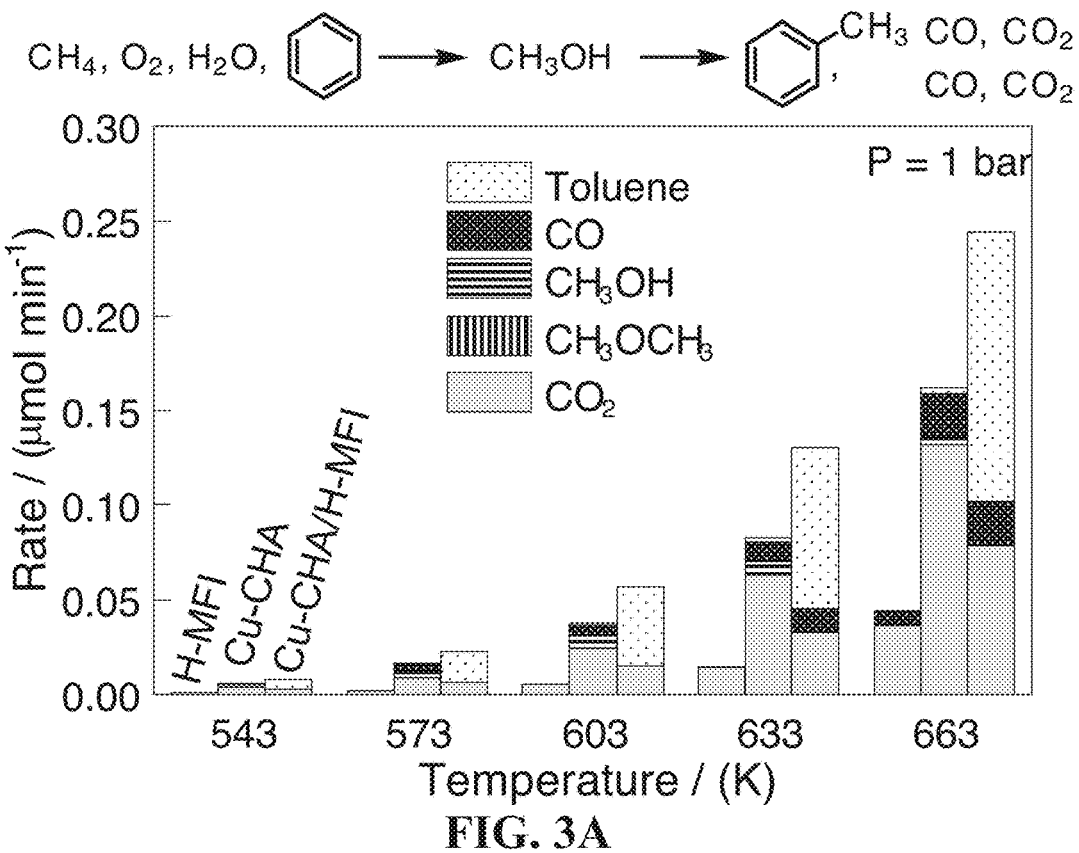
FIG. 3A shows, according to some embodiments, a comparison of the total rates of product formation across temperature.
Figure 3B:
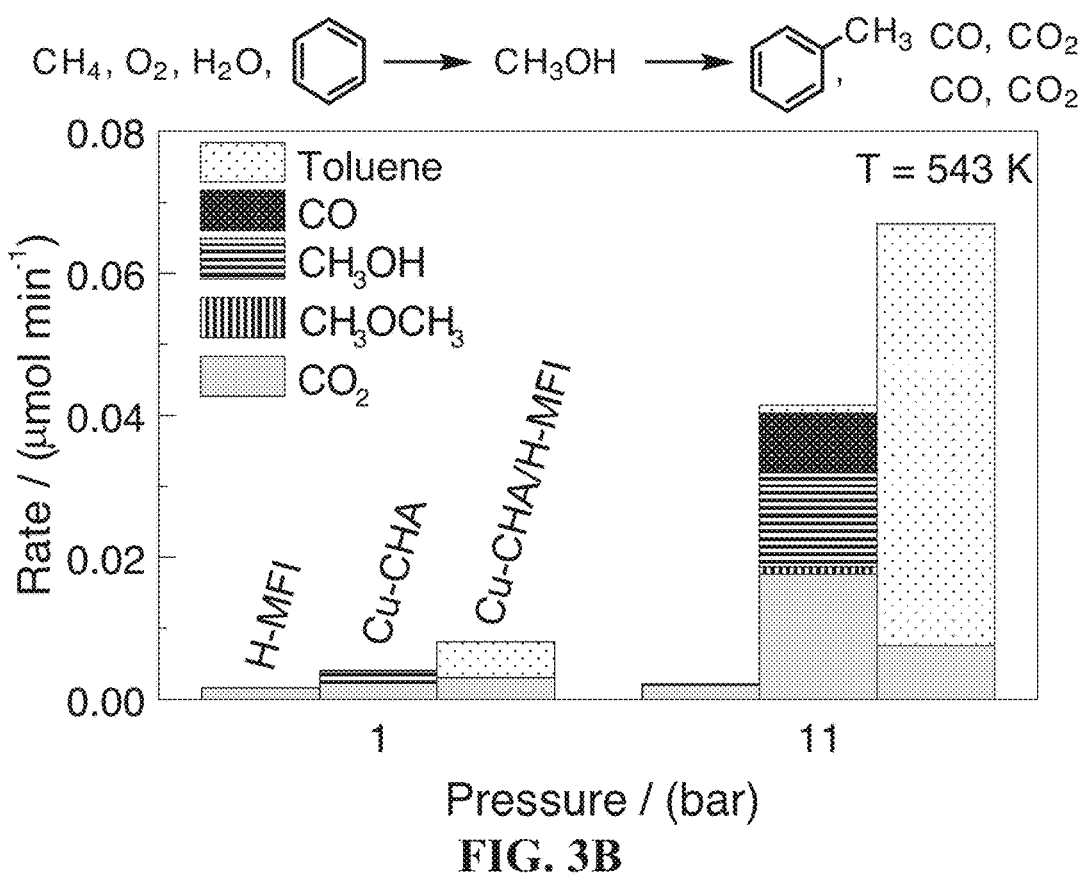
FIG. 3B shows, according to some embodiments, a comparison of the total rates of product formation across pressure.

FIGS. 3A-3B demonstrate that both Cu-CHA and H-MFI were significant for toluene formation across all temperatures and pressure studied. For FIGS. 3A-3B, catalyst composition and the alkylation feed mixture was 0.2625 g H-MFI-1, 0.0875 g Cu-CHA-1, and (0.0875 g Cu-CHA-1+ 0.2625 g H-MIF-2), 26.1 sccm, $x_{CH4}$=0.18, $xC_6H_6$=0.008, $xO_2$=0.001, $P_{H2O}$=3.1 kPa, bal He, where x indicates mole fraction. When pressurizing, water partial pressure remained unchanged because it was introduced by a saturator, while other reactants increased proportionally. The reaction schematic shown above FIGS. 3A and 3B demonstrates potential sources of product formation based where C's are indicative of source of C ($CH_4$ or benzene) for observed products.

Figures 12A, 12B:
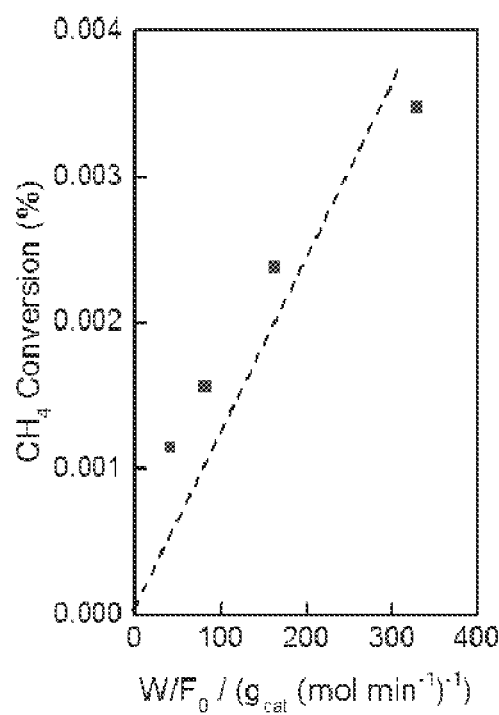
FIG. 12A shows, according to some embodiments, a table of parameters used for verification of absence of heat and mass transfer gradients.
FIG. 12B shows, according to some embodiments, a plot of $CH_4$ conversion versus contact time for Cu-CHA-1 and H-MFI-2.
Figure 13:
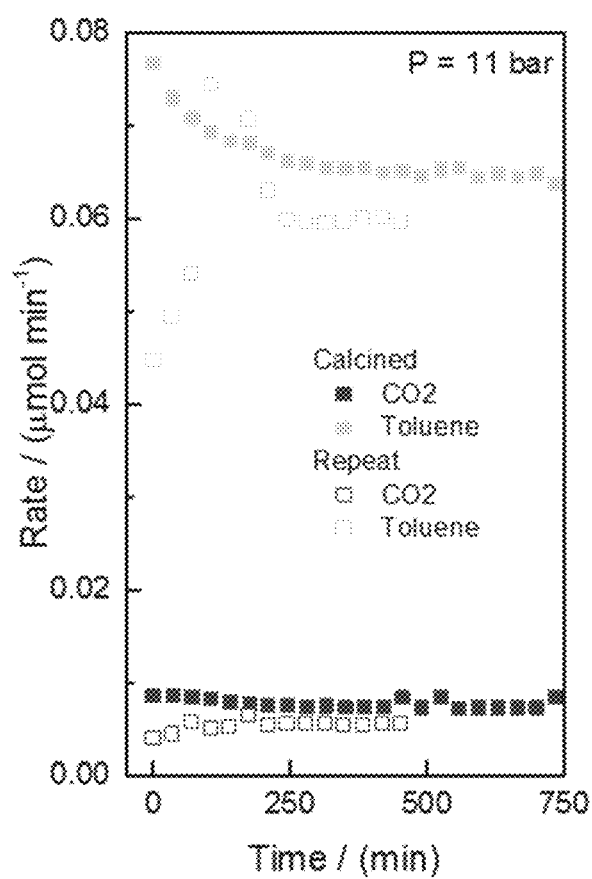
FIG. 13 shows, according to some embodiments, rates of product formation over Cu-CHA/H-MFI versus time-on-stream
Figure 14A:
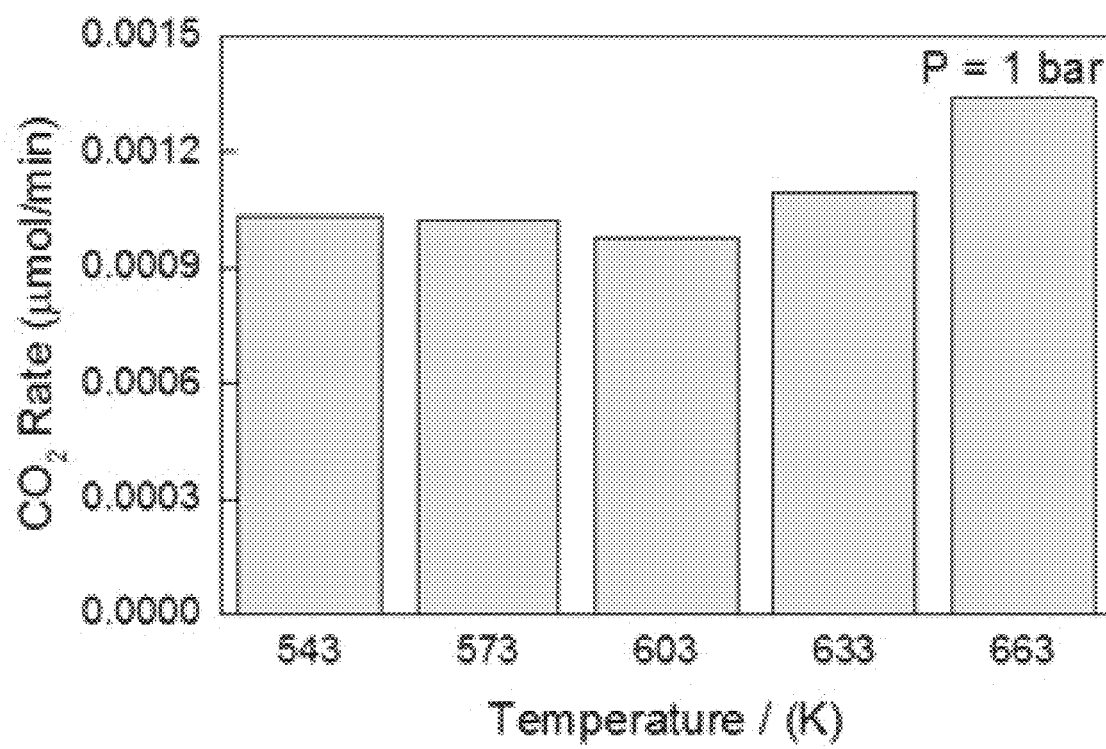
FIG. 14A shows, according to some embodiments, rates of $CO_2$ formation in the absence of catalyst across pressure.
Figure 14B:
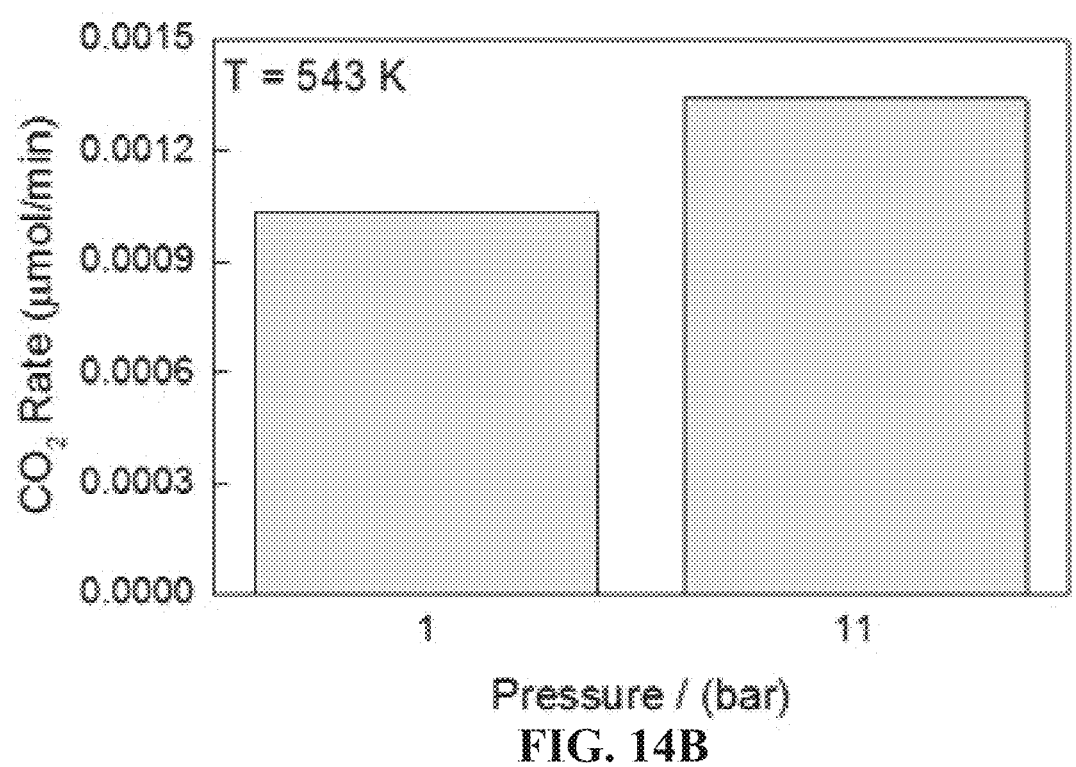
FIG. 14B shows, according to some embodiments, rates of $CO_2$ formation in the absence of catalyst across temperature.

Reaction rates were measured in the absence of heat and mass transfer limitations (see FIGS. 12A-12B). For FIG. 12B, the catalyst composition and feed mixture was (0.0875 g Cu-CHA-1+0.2625 g H-MFI-2), 543 K, 1 bar, 26.1–209 sccm, $P_{CH4}$=18 kPa, $P_{O2}$=0.09 kPa, $P_{H2O}$=3.1 kPa, $P_{C6H6}$=0.80 kPa, bal He. Stable and repeatable product formation rates were observed for at least 12 hours on stream (see FIG. 13). FIG. 13 demonstrates that stable rates were observed for at least 12 hours. For FIG. 13, the catalyst composition and feed mixture was (0.0875 g Cu-CHA-1+ 0.2625 g H-MFI-2), 543 K, 26.1 sccm, $xCH_4$=0.008, $xC_6H_6$=0.008, $xO_2$=0.001, $P_{H2O}$=3.1 kPa, bal He. Catalysts were calcined at 823 K under dry air for 8 hours prior to testing. Rates of product formation were presented as the absolute rates observed to enable direct comparison of these three catalysts. The catalyst loading of the individual H-MFI and Cu-CHA catalysts beds were the same as in the intimately mixed catalyst bed. Toluene was not observed in the absence of catalyst under the same feed and reactor conditions (see FIGS. 14A and 14B). For FIGS. 14A-14B, the feed mixture was 26.1 sccm, $xCH_4$=0.18, $xC_6H_6$=0.008, $xO_2$=0.001, $P_{H2O}$=3.1 kPa, bal He where x indicates mole fraction. When pressurizing, water partial pressure remained unchanged because water is introduced by a saturator, all other reactants increased proportionally. In the absence of either Cu-CHA or H-MFI, low rates of toluene formation were observed over H-MFI for P>1 bar and over Cu-CHA for T≥633 K or P>1 bar (see FIGS. 3A-3B). These rates of formation of toluene were much lower than those observed over Cu-CHA/H-MFI. It was hypothesized that the observed toluene formation over Cu-CHA was a result of surface protons catalyzing aromatic alkylation since benzene cannot access the pores of Cu-CHA.

Figure 15:
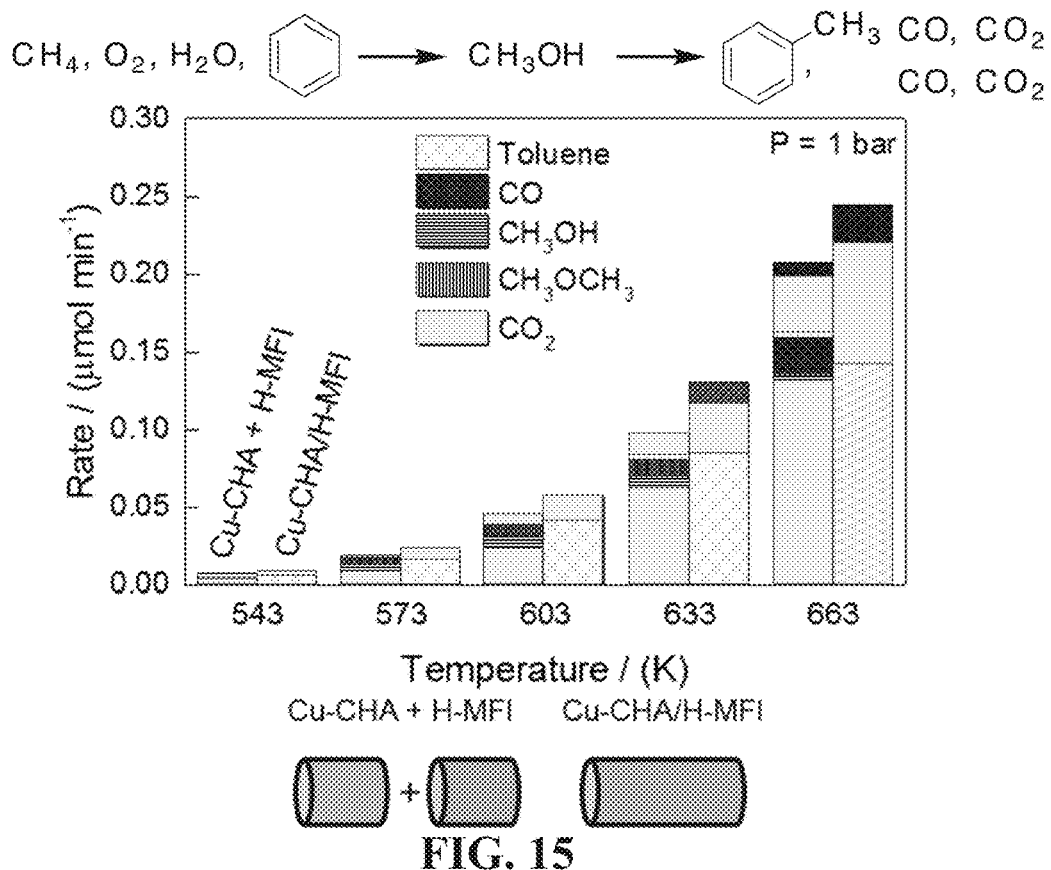
FIG. 15 shows, according to some embodiments, a comparison of tandem oxidation and alkylation rates from the addition of individual beds of Cu-CHA and H-MFI to an intimately mixed bed of Cu-CHA/H-MFI.

Upon closer inspection of FIGS. 3A-3B, the total rate of product formation was consistently higher over Cu-CHA/H-MFI than over either H-MFI or Cu-CHA or the addition of the rates of production formation over each of H-MFI and Cu-CHA (see FIG. 15). For FIG. 15, the catalyst composition and feed mixture was 0.2625 g H-MFI-1, 0.0875 g Cu-CHA-1, and (0.0875 g Cu-CHA-1+0.2625 g H-MFI-2), 26.1 sccm, $xCH_4$=0.18, $xC_6H_6$=0.008, $xO_2$=0.001, $P_{H2O}$=3.1 kPa, bal He. FIG. 15 demonstrates that across all temperatures, there is a greater rate of product formation for Cu-CHA/H-MFI than from the addition of the rates of product formation over individual Cu-CHA and H-MFI beds. It was hypothesized that the oxidation of benzene to CO and $CO_2$ contributed to these observed rates, in addition to the already expected over oxidation of $CH_4$ to $CO_2$. Thus, while the rate of toluene formation over Cu-CHA/H-MFI was similar to the total rate of product formation over Cu-CHA, a direct comparison could not be made due to differing amounts of CO and $CO_2$ stemming from benzene over these catalysts. To study complete $CH_4$ and benzene oxidation reactions in greater detail, the rates of product formation were observed over the same catalyst beds in the absence of benzene and $CH_4$, respectively.

Figure 4A:
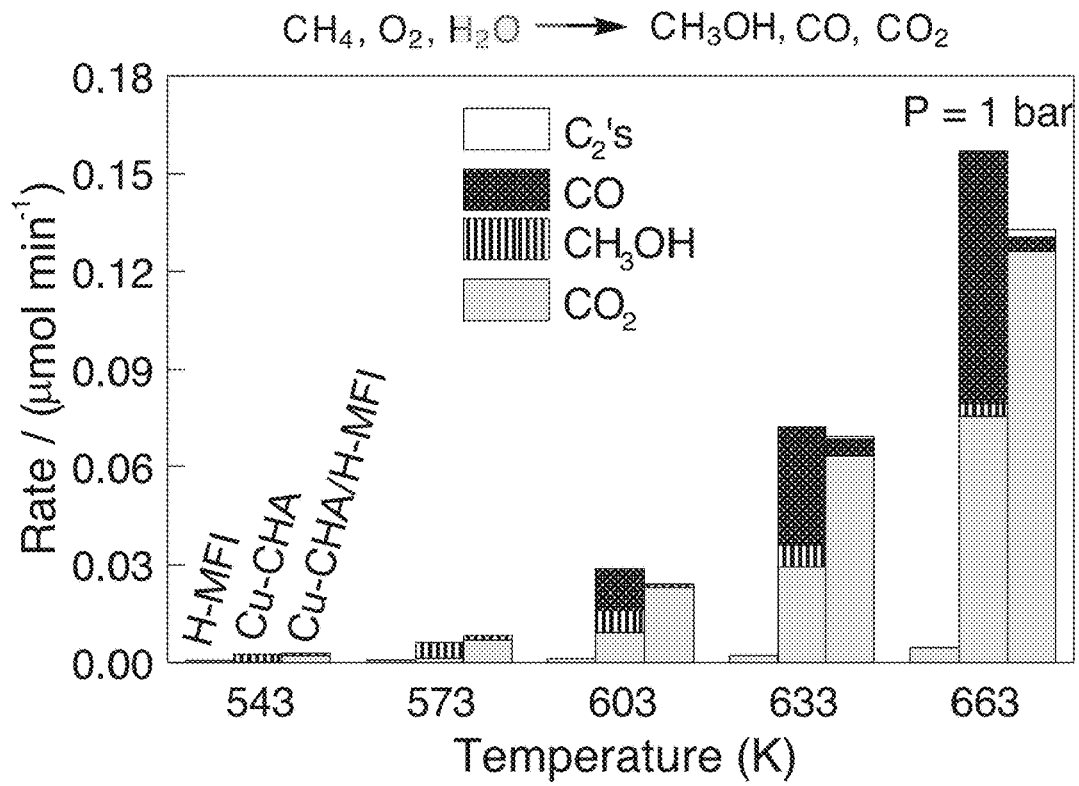
FIG. 4A shows, according to some embodiments, a comparison of the total rates of conversion and product formation under partial methane oxidation flows.

FIG. 4A demonstrates that, in the absence of benzene (feeding $CH_4/H_2O/O_2$), the activation of the C—H bond of $CH_4$ originates primarily over Cu-CHA. Across all temperatures, the total rate of C—H activation was similar between Cu-CHA and Cu-CHA/H-MFI. Further, the rate of C—H activation over MFI was negligible over 543-663 K, in comparison to the rates of C—H activation versus Cu-CHA. The absence of significant $CH_3OH$ formation between Cu-CHA and Cu-CHA/H-MFI was attributed to the added catalyst through which $CH_3OH$ travelled, increasing the probability of over oxidation events occurring homogeneously or over H-MFI.

Figure 4B:
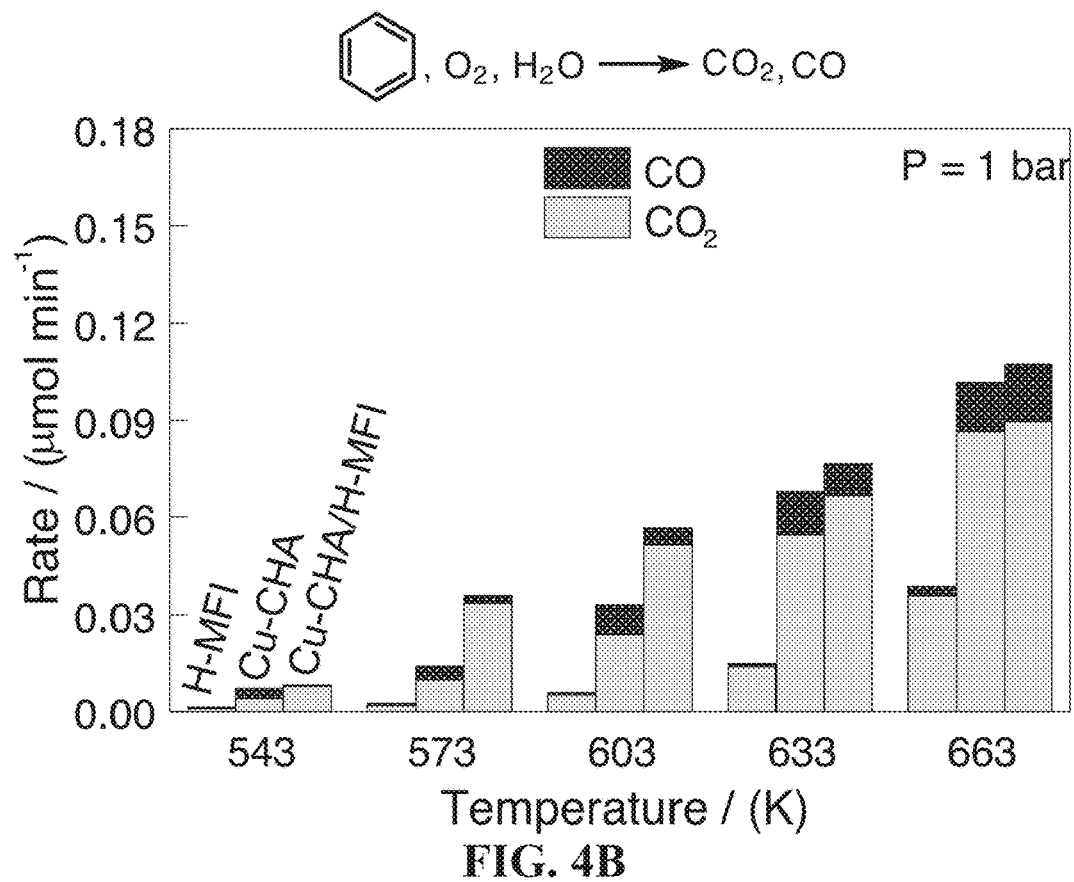
FIG. 4B shows, according to some embodiments, a comparison of the total rates of conversion and product formation under benzene oxidation flows.

FIG. 4B demonstrates how benzene oxidation contributes to the rates of CO and $CO_2$ formation in the absence of $CH_4$ (feeding $C_6H_6/H_2O/O_2$). Across all three catalyst beds, CO and $CO_2$ were the primary products observed. Because these rates of product formation were on similar scales to those observed when co-feeding $CH_4/H_2O/O_2$ (see FIG. 4A), the contribution of benzene oxidation to CO and $CO_2$ product formation rates under tandem oxidation and alkylation conditions was considered. It was unknown to what extent Cu-CHA and H-MFI each contributed to the observed rates of product formation over Cu-CHA/H-MFI because the sum of the rates over the individual catalyst beds of H-MFI and Cu-CHA was not equal to the rates over Cu-CHA/H-MFI. The catalyst composition and feed mixture in FIGS. 4A-4B was 0.2625 g H-MFI-1, 0.0875 g Cu-CHA-1, and (0.0875 g Cu-CHA-1+0.2625 g P=1 bar, 26.1 sccm, $P_{CH4}$=18 kPa, $P_{O2}$=0.09 kPa, $P_{H2O}$=3.1 kPa, $P_{C6H6}$=0.80 kPa, bal. He. The reaction schematics shown above FIGS. 4A-4B demonstrate potential sources of product formation based where C's are indicative of source of C ($CH_4$ or benzene) for observed products.

Given the significance of benzene oxidation, an isotope switching experiment with $^{13}C_6H_6$ under tandem oxidation and alkylation conditions (co-feed of $CH_4/O_2/H_2O/C_6H_6$) over Cu-CHA/H-MFI revealed benzene oxidation was the primary source of CO and accounted for more $CO_2$ as temperature increased. At 543 K and 1 bar, benzene accounted for 85% of CO and 19% of $CO_2$ observed. At 603 K and 1 bar, benzene accounted for 85% of CO and 42% of $CO_2$. These results were used to remove the contribution of benzene oxidation to CO and $CO_2$ formation rates over Cu-CHA/H-MFI and enable direct comparison of the rates of product formation from $CH_4$-to-$CH_3OH$ over Cu-CHA to the rates of product formation from tandem oxidation and alkylation over Cu-CHA/H-MFI. Kinetic data in combination with these results was used to estimate the contribution of benzene oxidation at conditions not specifically tested.

Figure 5A:
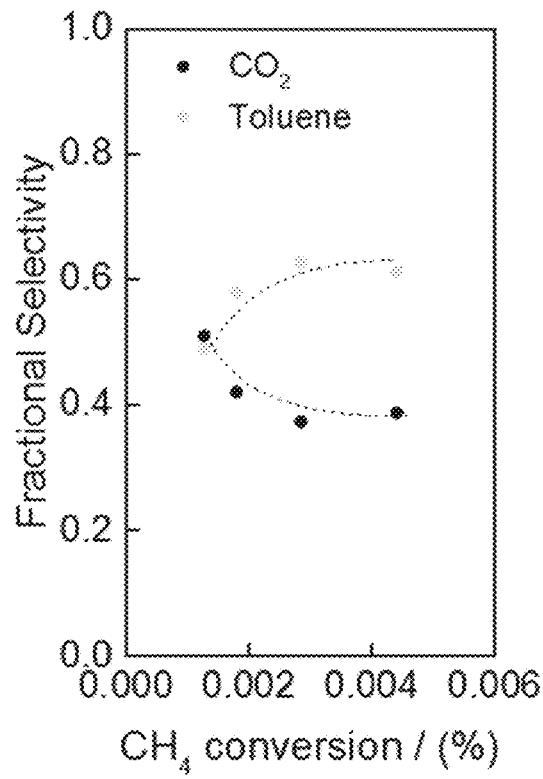
FIG. 5A shows, according to some embodiments, product selectivity versus conversion.

To gain further insight into the origins of product formation and the role of each reactant during tandem partial oxidation and alkylation, kinetic experiments at 543 K were completed by varying the total flow and partial pressures of $CH_4$, $O_2$, and benzene fed to Cu-CHA/H-MFI (see FIGS. 5A-5D). The catalyst composition and feed mixture in FIGS. 5A-5D was (0.0875 g Cu-CHA-1+0.2625 g H-MFI-2), T=543 K, P=1 bar, 26.1 sccm, 3.2 kPa $H_2O$, 0.09 kPa $O_2$, 18 kPa $CH_4$, 0.80 kPa benzene, bal He, except as noted. Analysis of a plot of selectivity versus conversion demonstrated product formation proceeded by a combination of sequential and parallel reaction pathways (FIG. 5A). The parallel reaction pathway was plausibly attributed to two sources: (1) parallel formation of $CO_2$ from benzene and (2) parallel formation of $CO_2$ and toluene from $CH_3OH$. The presence of a sequential pathway is consistent with $CH_4$ activation first proceeding to $CH_3OH$ and then to toluene and $CO_2$. Based on this reaction pathway, at low conversion, increasing selectivity to $CO_2$ with decreasing $CH_4$ conversion is explained by the persistence of oxidation of benzene to $CO_2$ while the rates of $CO_2$ and toluene formation from $CH_3OH$ have decreased as a result of the reduced accumulation of methanol.

Figure 5B:
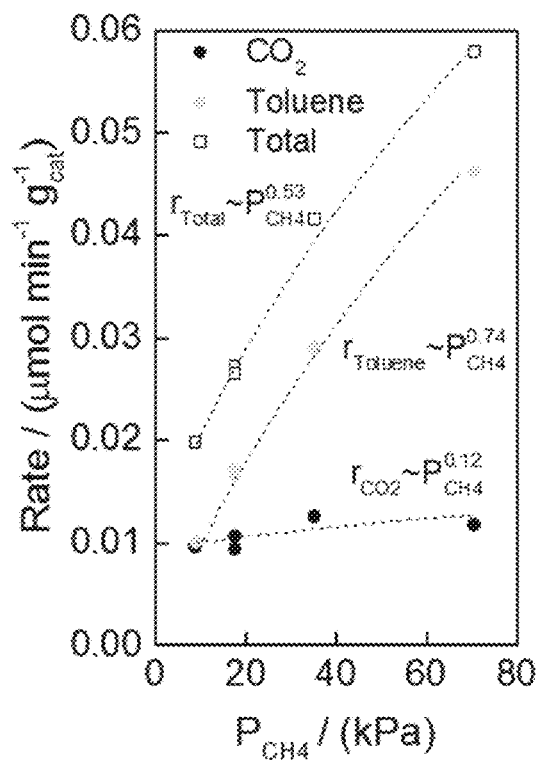
FIG. 5B shows, according to some embodiments, product formation rates versus $P_{CH4}$.
Figure 5C:
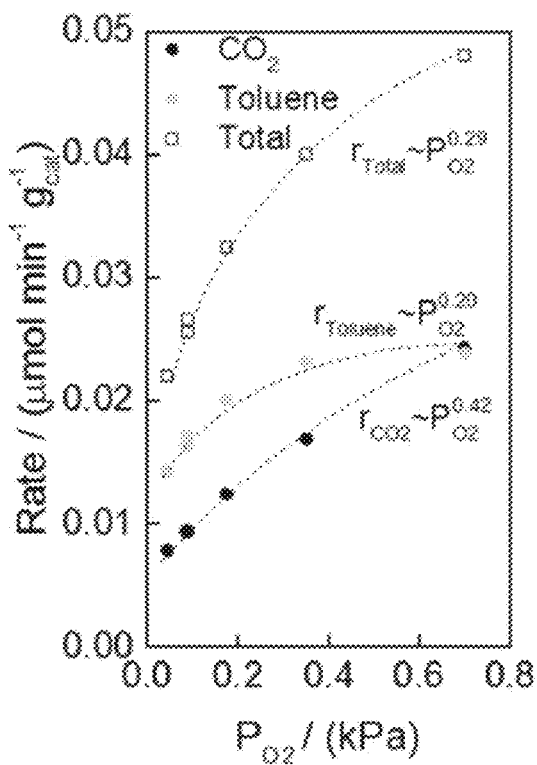
FIG. 5C shows, according to some embodiments, product formation rates versus $P_{O2}$.
Figure 5D:
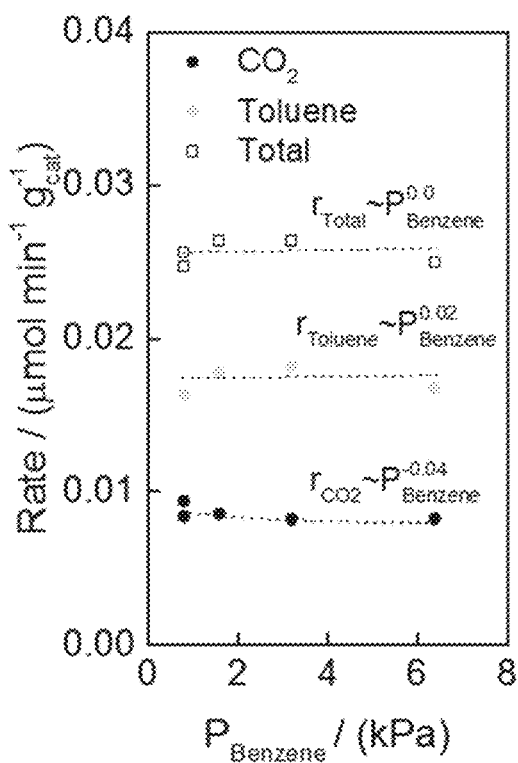
FIG. 5D shows, according to some embodiments, product formation rates versus $P_{benzene}$.
Figure 6:
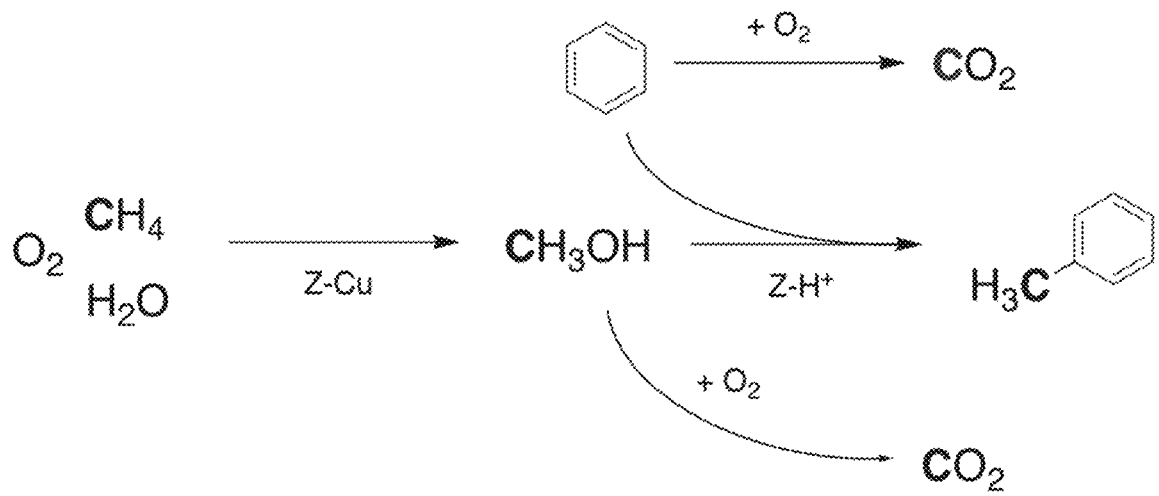
FIG. 6 shows, according to some embodiments, a schematic of a hypothesized reaction pathway in the methane partial oxidation/aromatic alkylation mixed system.

$CH_4$ and $O_2$ partial pressure analyses over Cu-CHA/H-MFI revealed C—H scission of $CH_4$ was Fate-determining and the relatively fast interception of $CH_3OH$ with benzene prior to over oxidation to $CO_2$ (FIGS. 5B and 5C, respectively). A near first order dependence of the rate of toluene formation on $P_{CH4}$ implied C—H scission of $CH_4$ as the rate-determining step. A 0.4 order dependence for the rate of $CO_2$ formation on $P_{O2}$ was consistent with the relatively fast interception of $CH_3OH$ by benzene as compared to over oxidation to $CO_2$ because this order dependence was less than the observed first order dependence of the rate of $CO_2$ formation on $P_{O2}$ under methanol synthesis conditions over Cu-CHA. Finally, a zero-order dependence of the rates of product formation on $P_{benzene}$ (see FIG. 5D) demonstrated benzene alkylation was not rate-limiting nor inhibiting reaction pathways that were necessary to allow for the formation of $CH_3OH$. These observations are summarized by the proposed reaction pathway in FIG. 6, where initial $CH_4$ activation forms $CH_3OH$ that can either alkylate benzene to form toluene or be over oxidized to form $CO_2$. $CO_2$ is also formed via benzene oxidation in a parallel pathway. Deleterious $CO_2$ formation from methanol oxidation is minimized by intermediate scavenging to form alkylated aromatics, thus decreasing $CO_2$ yields, and direct benzene oxidation pathways can be mitigated by modification of catalyst morphology and gas phase compositions. CO formation is hypothesized to form by the same reaction pathways as $CO_2$.

Figure 7A:
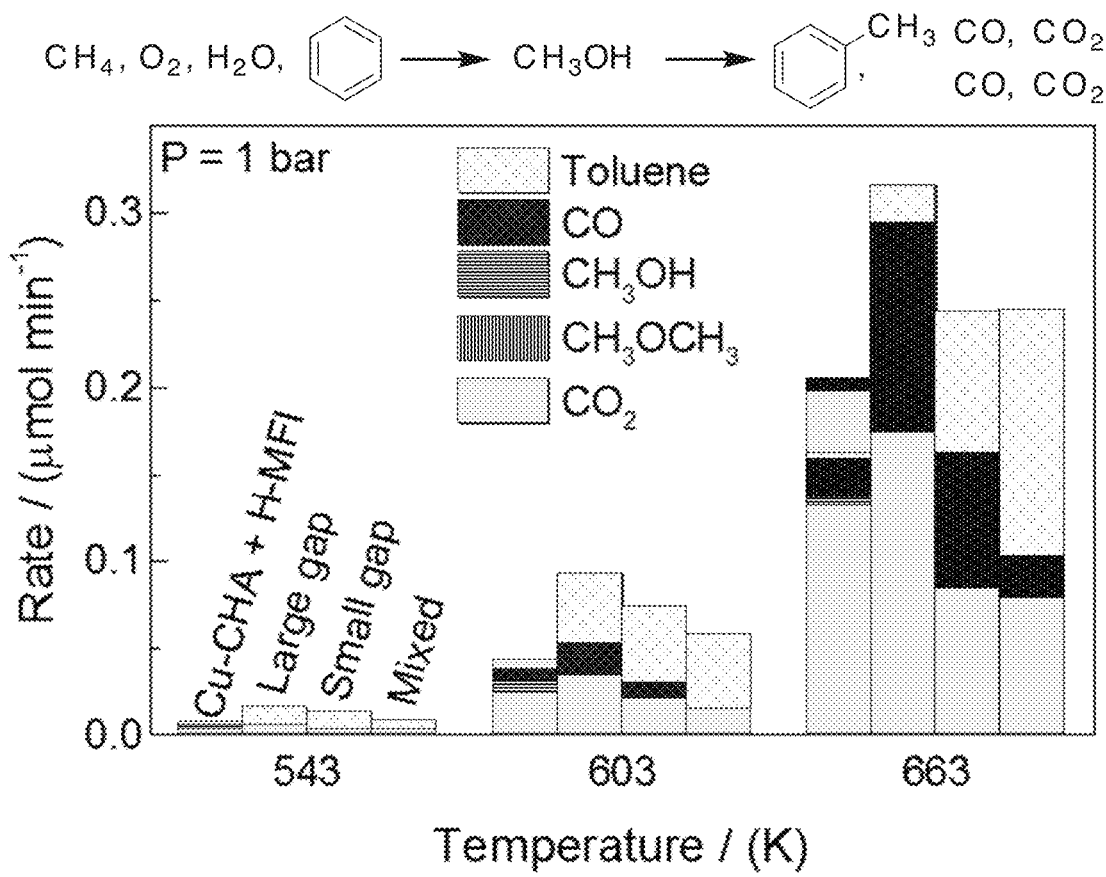
FIG. 7A shows, according to some embodiments, a comparison of the total rates of product formation across temperature.
Figure 7B:
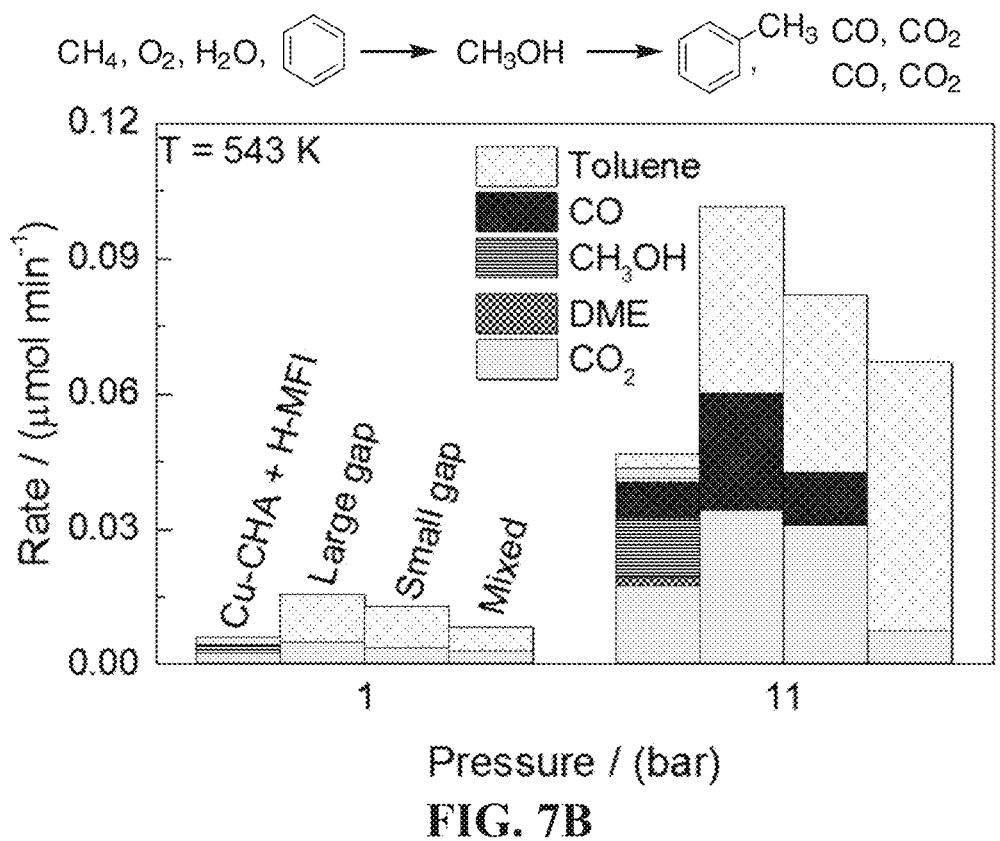
FIG. 7B shows, according to some embodiments, a comparison of the total rate of product formation across and pressure.

Next, placing separate beds of Cu-CHA and H-MFI in series separated by quartz wool demonstrated that intimate mixing of Cu-CHA and H-MFI obtained the optimum selectivity (see FIGS. 7A-7B). In FIGS. 7A-7B, "Cu-CHA+H-MFI" corresponds to the addition of rates of individual beds of Cu-CHA and H-MFI where these catalysts were tested separately, "Large gap" corresponds to a 3 cm quartz wool plug between beds, and "Small gap" corresponds to a 1 cm quartz wool plug. (0.0875 g Cu-CHA-1 and 0.2625 g H-MFI-2), 26.1 sccm, $xCH_4$=0:18, $xC_6H_6$=0.008, $xO_2$=0.001, $P_{H2O}$=3.1 kPa, bal He, where x indicates mole fraction. When pressurizing, water partial pressure remained unchanged because it was introduced by a saturator, while other reactants increased proportionally. The reaction schematics above FIGS. 7A and 7B demonstrate potential sources of product formation based where C's are indicative of source of C ($CH_4$ or benzene) for observed products.

The rates of production formation over separate beds in series were compared to intimately mixed Cu-CHA and H-MFI and to the simple addition of product formation rates from individual. Across a range of temperature and pressures, two things stood out as the two catalyst beds were brought into closer contact: (1) the rate of toluene formation increased and (2) the rates of $CO_2$ and CO formation decreased. Consequently, intimately mixed Cu-CHA and H-MFI yielded the highest toluene selectivity of all catalyst configurations under identical conditions. These observations were rationalized by the increased distance $CH_3OH$ must be transported to be brought into contact with H-MFI with the separated beds, thereby increasing the number of homogeneous over oxidation events of $CH_3OH$ and reducing the amount of $CH_3OH$ available for benzene alkylation.

Figure 8A:
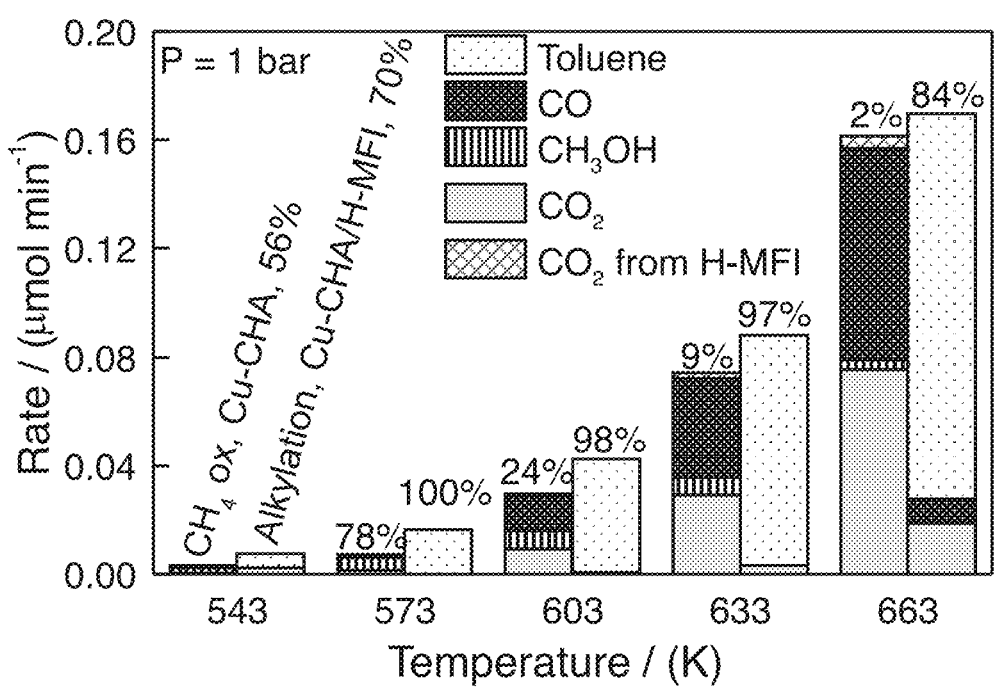
FIG. 8A shows, according to some embodiments, a comparison of rates of $CH_4$-to-$CH_3OH$ over Cu-CHA-1 to tandem oxidation and alkylation over Cu-CHA-1/H-MFI-2 across temperature.
Figure 8B:
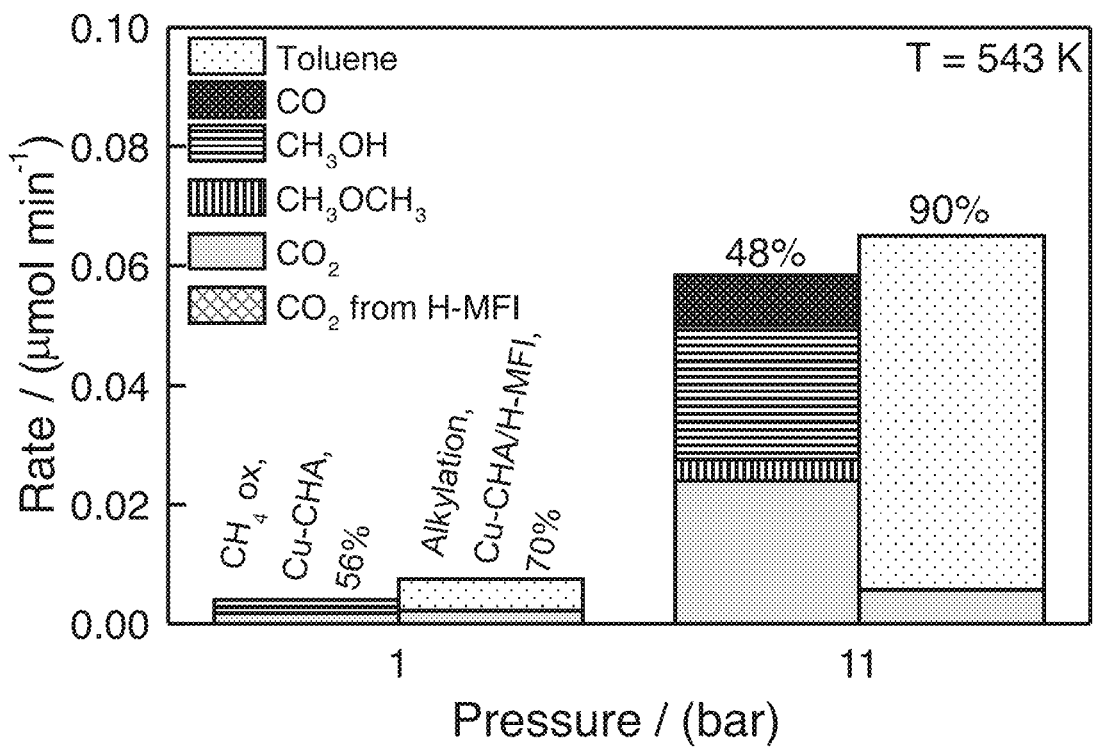
FIG. 8B shows, according to some embodiments, a comparison of rates of $CH_4$-to-$CH_3OH$ over Cu-CHA-1 to tandem oxidation and alkylation over Cu-CHA-1/H-MFI-2 across pressure.

Based upon the intimate mixing of Cu-CHA and H-MFI and knowledge of the origins of each product, $CH_4$-to-$CH_3OH$ conversion over Cu-CHA was compared to $CH_4$-to-$CH_3OH$-to-toluene conversion over Cu-CHA/H-MFI (see FIGS. 8A-8C) to demonstrate the efficacy of methanol scavenging. The results of the isotope labeling experiment plus kinetic experiments were used to remove the contribution of benzene, to $CO_2$ and CO formation rates in the tandem partial oxidation and alkylation system. First, FIGS. 8A and 8B demonstrate there was good agreement between the total rates of product formation over Cu-CHA and Cu-CHA/H-MFI, consistent with $CH_4$ activation occurring primarily over Cu-CHA as previously discussed, and enabling facile observation of the improvement in desirable product selectivity under tandem partial oxidation and alkylation conditions. In FIGS. 8A-8B, the numbers above each bar are the carbon-weighted selectivities for partial oxidation products. The slight differences in the total rate of C—H activation may have been a result of slight variations in Cu content between catalyst beds. The improvement in partial oxidation selectivity was highlighted at 663 K and 1 bar where there was 84% selectivity for toluene over Cu-CHA/H-MFI, in contrast to 2% selectivity for $CH_3OH$ over Cu-CHA. The high selectivity for toluene at increasing conversion was indicative of the relatively fast scavenging of $CH_3OH$ by toluene versus thermodynamically favorable deleterious over oxidation events with free gaseous $CH_3OH$.

Increasing pressure for catalytic $CH_4$-to-$CH_3OH$ conversion resulted in a small decrease in selectivity for $CH_3OH$ (see FIG. 8B), which was in contrast to stoichiometric processes where selectivity is often minimally affected. However, increasing pressure under tandem oxidation and alkylation conditions over Cu-CHA/H-MFI improved selectivity from 70% to 89%. This improved selectivity was explained by analysis of the total dependence on reactant partial pressures for each product (e.g., with $r_{product} \sim P_{CH4}{}^a P_{O2}{}^b$, the total order dependence is a+b). Because toluene had a total dependence of 0.94 versus 0.54 for $CO_2$, increasing the pressure increased the rate of toluene formation 75% more than the rate of $CO_2$ formation. In contrast, the rate of methanol formation had a total order dependence of 1.03 versus 1.14 for the rate of $CO_2$ formation under $CH_4$-to-$CH_3OH$ conditions over Cu-SSZ-13, consequently slightly favoring $CO_2$ formation at elevated pressures. Thus, under tandem partial oxidation and alkylation conditions, pressure provided another variable for optimizing process conditions for selective $CH_4$ oxidation that would otherwise be unavailable.

Figure 8C:
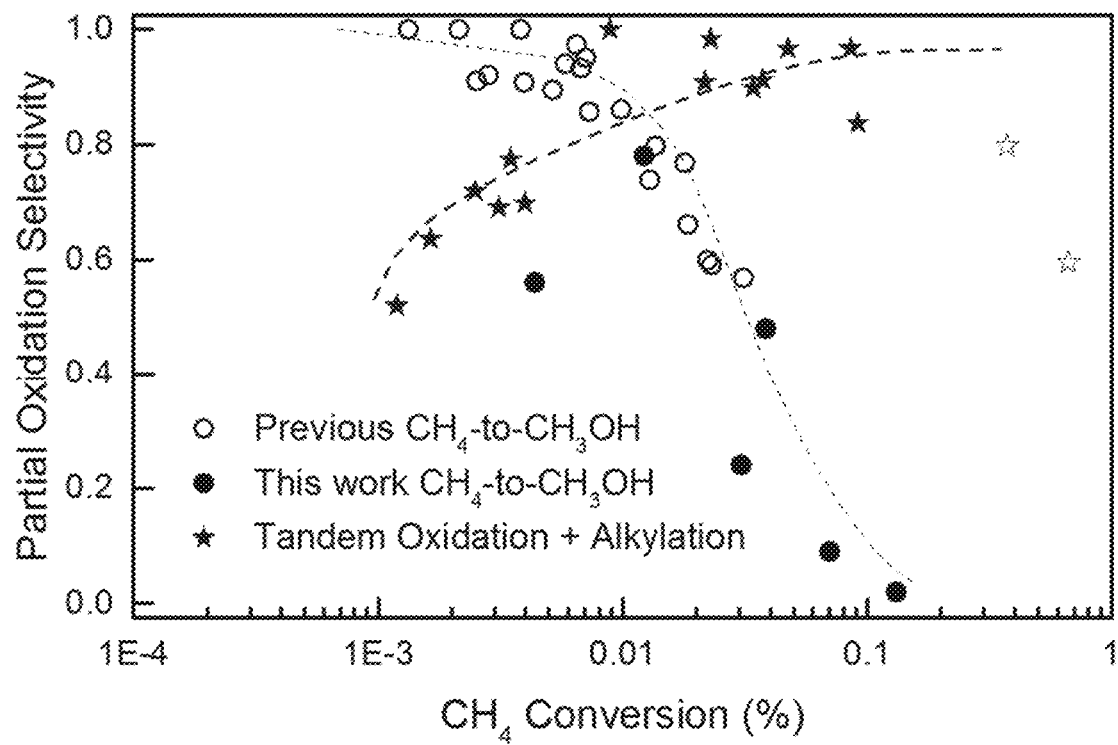
FIG. 8C shows, according to some embodiments, the selectivity for partially oxidized products versus conversion.

Based on these favorable results, plotting partial oxidation selectivity versus conversion demonstrated that the selectivity-conversion limit of $CH_4$ was circumvented by scavenging methanol (see FIG. 8C). In FIG. 8C, the "open circles" were previously reported, "solid circles" were from the compositions reported herein and generated by varying temperature and pressure as in FIG. 8A and FIG. 8B over 0.0875 g Cu-CHA-1. "Solid stars" were generated by altering temperature, pressure, total flow rate, catalyst loading and $P_{O2}$ over (0.0875 g Cu-CHA-1+0.2625 g H-MFI-1), (0.0875 g Cu-CHA-1+0.2625 g H-MFI-2), and (0.366 g Cu-CHA-2+1097 g H-MFI-3). "Open stars" increased $P_{O2}$ by 3× and 5×. Baseline flow conditions: 26.1 sccm, $xCH_4$=0.18, $xC_6H_6$=0.008, $xO_2$=0.001, $P_{H2O}$=3.1 kPa, bal He, where x indicates mole fraction. When pressurizing, water partial pressure remained unchanged because it was introduced by a saturator, while other reactants increased proportionally.

Figure 9A:
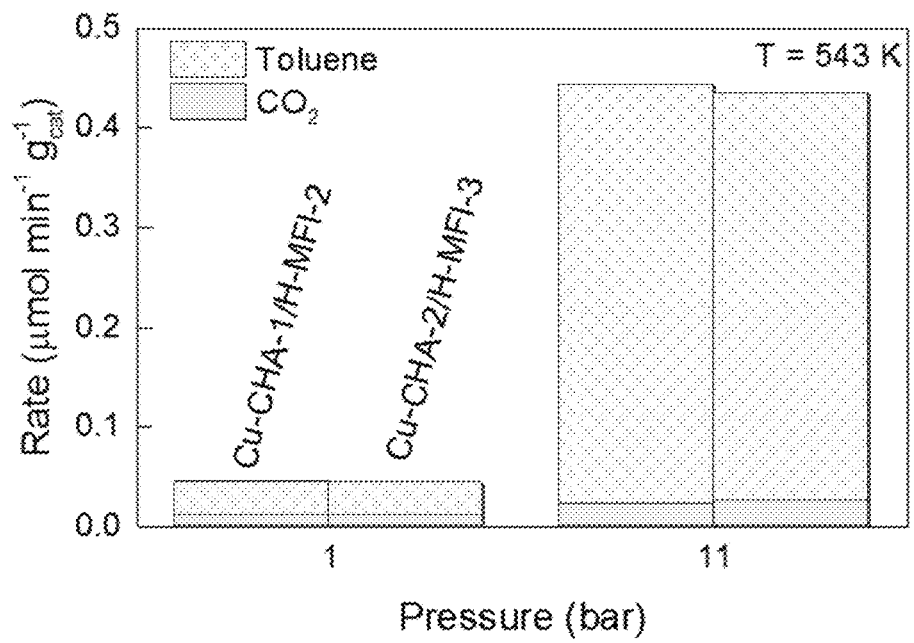
FIG. 9A shows, according to some embodiments, a comparison of rates of product formation of Cu-CHA-1/H-MFI-2 and Cu-CHA-2/H-MFI-3.
Figure 9B:
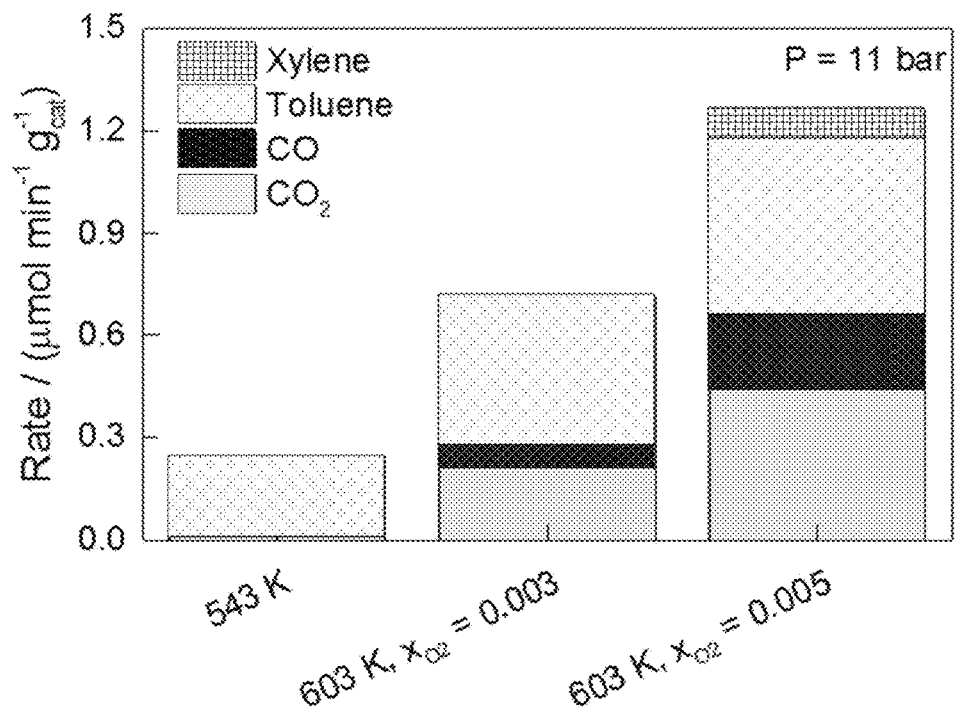
FIG. 9B shows, according to some embodiments, a comparison of rates of product formation rates across multiple conditions over Cu-CHA-2/H-MFI-3.

Data points presented were generated by altering contact time, temperature, pressure, and catalyst loading, as shown in FIG. 8D. Rates of product formation with increased catalyst loading are presented in FIGS. 9A-9B. $P_{O2}$ was increased by 3× and 5× for the points at 0.3% and 0.6% $CH_4$ conversion, respectively Immediately apparent was above 0.01% $CH_4$ conversion, selectivity for toluene was at least 80% while selectivity for $CH_4$-to-$CH_3OH$ over Cu-CHA dropped to <60%. It was hypothesized that the low selectivity for toluene observed below 0.01% $CH_4$ conversion was a result of the low rates of $CH_3OH$ formation at these conditions where the competition between over oxidation of $CH_3OH$ to $CO_2$ versus its diffusion to Brønsted acid sites in H-MFI became important. Implementation of a tandem partial oxidation and alkylation system enabled these results to surpass previously reported results for selectivity versus $CH_4$ conversion at mild conditions, while only requiring readily available $O_2$ and $H_2O$ for $CH_4$ activation.

These results warranted comparison to the best performing stoichiometric processes for $CH_4$-to-$CH_3OH$ conversion over Cu-exchanged zeolites and to other heterogeneous $CH_4$-to-$CH_3OH$ systems. Conventional systems have reported the optimization of an isothermal stoichiometric process over a Cu-FAU zeolite (Si/Al=2.6, Cu/Al=0.41, Cu wt. %=9.32) where the catalyst was first activated for 1 hour under $O_2$ and then exposed to $CH_4$ for 1 hour. Following, methanol was desorbed for 1 hour at 633 K with water vapor. Taking this process as a 3 hour cycle time, the optimized methanol yield was 2 $\mu mol_{CH3OH}$ min$^{-1}$ g$_{cat}{}^{-1}$ (~1400 $\mu mol_{CH3OH}$ mol$_{Cu}{}^{-1}$ min$^{-1}$, 93% selectivity). In comparison, the results reported herein are a greater yield for tandem oxidation and alkylation of 2.7 $\mu mol_{Toluene+Xylene}$ min$^{-1}$ g$_{Cu-CHA}{}^{-1}$ at 603 K and 11 bar (74% selectivity for toluene and xylene combined). Additionally, the Cu loading was an order of magnitude lower than that used for the optimized stoichiometric process, giving a rate of formation of 19,000 $\mu mol_{CH3OH}$ mol$_{Cu}{}^{-1}$ min$^{-1}$ that far exceeded the 1400 $\mu mol_{CH3OH}$ mol$_{Cu}{}^{-1}$ min$^{-1}$ reported for the optimized stoichiometric process.

This conversion and yield for tandem oxidation and alkylation was also comparable to the best performing heterogeneous catalysts for $CH_4$-to-$CH_3OH$ conversion. Greater than 75% $CH_3OH$ selectivity has been reported for heterogeneous catalysts at <2% $CH_4$ conversion. However, with the exception of Cu-exchanged zeolites, the remaining heterogeneous catalysts required expensive oxidants such as $H_2O_2$ or $N_2O$ or extreme conditions (e.g., P>140 bar), but the system reported herein simply required $O_2$, $H_2O$, and benzene as additional reactants and H-MFI as an additional catalyst at relatively mild conditions in comparison to these processes.

As demonstrated herein, the viability of product protection for $CH_4$ activation was achieved by first activating $CH_4$ over Cu-exchanged zeolites to produce $CH_3OH$ and then capturing $CH_3OH$ by aromatic alkylation over a proton-form zeolite. Control reactions and isotopically labeled benzene experiments demonstrated that benzene oxidation occurred in parallel to methane activation and contributed to the observed CO and $CO_2$ formation rates. Upon accounting for benzene oxidation, the rates of $CH_4$ activation were comparable between Cu-CHA and Cu-CHA/H-MFI across all conditions, but selectivity for desirable products was markedly improved by chemically scavenging methanol. High selectivity towards desirable products was maintained, even above 0.1% $CH_4$ conversion where selectivity for $CH_4$-to-$CH_3OH$ processes deteriorate. A toluene and xylene, yield of 2.7 $\mu mol_{Toluene+Xylene}$ $min^{-1} g_{Cu-CHA}^{-1}$ at 603 K and 11 bar was determined, which was greater than an optimized stoichiometric $CH_4$-to-$CH_3OH$ system. Product protection is therefore an area of research to enable $CH_4$ activation, especially in the area of process optimization and catalyst design. Of particular interest are designing catalysts to reduce benzene oxidation and further limit $CH_3OH$ diffusion pathways. The successful product protection process described herein meets several factors: the catalysts are designed to minimize the gaseous lifetime of $CH_3OH$; scavenging reaction reactants and products are resistant to complete oxidation and do not interfere with partial methane oxidation to methanol; complete $CH_4$ oxidation does not occur over the catalyst designed to scavenge methanol; and the rate of the scavenging reaction is greater than the rate of methanol formation so that the scavenging reaction is not rate-limiting. This example provides a pathway towards achieving industrially relevant product selectivities at desirable $CH_4$ conversions.

Example 2

The following example describe the synthesis and characterization of the first catalyst and the second catalyst.

Cu-SSZ-13 was synthesized in a one-pot method via the use of tetraethylenepentamine (TEPA). Copper sulfate pentahydrate (98% trace metals basis, Sigma-Aldrich) was first dissolved in water followed by the addition of TEPA (technical grade, Sigma-Aldrich) and stirred for 1 hour before the addition of N,N,N-trimethyl-1-adamantanamine hydroxide solution (TMAdaOH, 25 wt. % in $H_2O$, Sachem). Following, aluminum hydroxide ($Al(OH)_3$, 80.3 wt. %, SPI Pharma 0250) was dissolved in the solution before fumed silica (Sigma-Aldrich, 99.8%) was added. The final composition of the mixture was 1 $SiO_2$: 0.07 $Al(OH)_3$:0.4 TMAdaOH: 44 $H_2O$: 0.01 $CuSO_4$: 0.011 TEPA. The solution was stirred at room temperature for 2 hours, transferred to four 23-mL Teflon-lined stainless steel autoclaves (No. 4749, Parr Instruments) and subjected to hydrothermal treatment at 433 K for 5 days in an oven under autogenous pressure and rotation (60 rpm). After hydrothermal treatment, the product was separated from the mother liquor by centrifugation, washed several times with distilled $H_2O$ until pH<9 and dried overnight at 393 K. The zeolite was calcined under dry air (Dry Size 300, Airgas) with the following temperature profile: heat 1 K $min^{-1}$ to 423 K and hold for 1 hour at 423 K, heat 1 K $min^{-1}$ to 623 K and hold for 1 hour at 623 K, and lastly heat 1 K $min^{-1}$ to 853 K and hold for 10 hours.

H-MFI was synthesized according to the following procedure: To 41.343 g water, 6.663 g tetrapropylammonium hydroxide (TPAOH, 40 wt % in water, SACHEM) was added and stirred for 15 minutes. Following, 0.135 g aluminum hydroxide (SPI Pharma 250) was added followed by 2.25 g sodium hydroxide solution in water (NaOH, Sigma-Aldrich, 23.0 wt. % in water). The mixture was stirred for at least 10 minutes. Then, 2.60 g fumed silica (Cab-o-Sil M5) was slowly added and shaken vigorously. The final gel composition was 1 $SiO_2$: 0.04 $Al(OH)_3$:0.3 TPAOH: 0.3 NaOH. The gel was allowed to homogenize and age with stirring for 16 hours before being transferred to 23-mL mL Teflon-lined stainless steel autoclaves (No. 4749, Parr instruments) and subjected to hydrothermal treatment under static conditions at 453 K for 2 days in an oven under autogenous pressure. After hydrothermal treatment, the product was separated from the mother liquor by centrifugation, washed several times with distilled $H_2O$ until pH<9 and dried overnight at 393 K. The zeolite was calcined under dry air (Dry Air Size 300, Airgas) with the following temperature profile: heat 1 K $min^{-1}$ to 423 K and hold for 1 hour at 423 K, heat 1 K $min^{-1}$ to 623 K and hold for 1 hour at 623 K, and lastly heat 1 K $min^{-1}$ to 853 K and hold for 10 hours.

Following calcination, to remove Na, 1 g of zeolite was stirred in 60 mL of a 1.0 M solution of ammonium nitrate (≥99%, Sigma-Aldrich) for 16 hours at room temperature. The suspension was filtered at room temperature, rinsed with 300 mL of deionized. $H_2O$, and the recovered zeolite was immediately subjected to the same ion exchange twice more under the same conditions. Following, the zeolite was dried overnight at 393 K in stagnant air and calcined following the same profile described above.

The first catalyst and the second catalyst were characterized using elemental analysis. Copper, sodium, and aluminum contents were determined using inductively coupled plasma atomic emission spectroscopy (ICP-AES, Agilent 5100) or inductively coupled plasma mass spectrometry (ICP-MS, Agilent 7900). 5-10 mg of zeolite were placed in a polyethylene microfuge tube (1.5 mL) and digested in 20 microliters of hydrofluoric acid (48 wt. %, trace metals basis, Sigma-Aldrich) for 2 hours. The hydrofluoric acid solution was diluted to a total mass of 10.0 g using 2 wt. % aqueous nitric acid ($HNO_3$) (veritas purity, GFS Chemicals). When using ICP-MS, 1 mL of these solutions were diluted once more to 10 mL solution total. A six-point calibration curve was built using ICP standard solutions of 1,000 ppm Cu in 2 wt. % $HNO_3$ 1,000 ppm Al in 2 wt. % $HNO_3$ and 1,000 ppm Na in 2 wt. % $HNO_3$. All standard solutions were purchased from Sigma-Aldrich (TraceCERT).

The molar ratios of $Si/Al_{tot}$ and $Cu/Al_{tot}$ in the catalysts were calculated as follows: The unit cell of a zeolite, is given by:

$$H_x^+ Na_y^+ Cu_z^{2+}(AlO_2)_n^-(SiO_2)_m(H_2O)_k$$

where subscripts refer to the molar ratios of each component within the unit cell of a zeolite. Local charge balance was assumed to occur within the zeolite, requiring x=n−2−y.

From the unit cell given above, the mass balance of the unit cell is given by the following equation on a per gram zeolite basis:

$$1 = a\frac{g\,SiO_2}{g\,zeolite} + b\frac{g[AlO_2]^-}{g\,zeolite} + c\frac{g\,Cu^{2+}}{g\,zeolite} + d\frac{g\,Na^+}{g\,zeolite} + e\frac{g\,H^+}{g\,zeolite} + f\frac{g\,H_2O}{g\,zeolite}$$

where each coefficient represents the weight percent of each species. The weight percent of Al, Cu and Na were directly calculated using ICP-AES, allowing b, c, and d to be determined. Converting the weight percentages of Al, Cu and Na to mole percentages per grain zeolite, e was then calculated using the local charge balance of cations on the zeolite framework. The weight percentage of $H_2O$ (f) was assumed to be equal to the weight percentage of $H_2O$ in the zeolite framework unit cell (2-7 wt %). The mass balance was then solved for the weight percentage of $SiO_2$ (a).

$Si/Al_{tot}$ was calculated by $$\frac{Si}{Al_{tot}} = \frac{a}{b}\frac{m_{AlO_2}}{m_{SiO_2}} \times \frac{1\,mol\,Si}{1\,mol\,SiO_2} \times \frac{1\,mol\,AlO_2}{1\,mol\,Al}$$

where $m_i$ is the molar mass of element i.

$Cu/Al_{tot}$ was calculated by $$\frac{Cu}{Al_{tot}} = \frac{c}{b}\frac{m_{AlO_2}}{m_{Cu}} \times \frac{1\,mol\,AlO_2}{1\,mol\,Al}$$

The crystal structures of zeolite catalysts were determined from powder x-ray diffraction patterns collected using a Bruker D8 diffractometer using Cu-Kα, radiation (λ=1.5418 Å, 40 kV, 40 mA). Data were recorded in the range of 3-40 2θ with an angular step size of 0.02° and a rate of 4° min$^{-1}$.

Scanning electron microscopy was performed on a Zeiss Merlin High-resolution SEM. Samples were crushed into a fine powder and loaded on to carbon black tape. Micrographs were collected at 3.0 kV, 100 pA, and 6.7 mm WD with the HE-SE2 detector in High Resolution column mode.

Example 3

The following example describes the experimental apparatus used for the partial oxidation of a reactant and the coupling reaction of the intermediate resulting from the partial oxidation with a co-reagent.

Reactions were conducted in a continuous, tubular flow reactor (304 stainless steel tube, O.D. 0.25 in, I.D. 0.18). The reactor tube was mounted inside a single-zone furnace (850 W/115V, Applied Test Systems Series 3210). Temperature was controlled using a thermocouple (Omega, model TJ36-CASS-116U) mounted slightly downstream of the catalyst, bed connected to a temperature controller (Digi-Sense model 68900-10). The mixture of a copper-exchanged zeolite and a proton-form zeolite were mixed in a ratio of 1:3 by weight, ground with a mortar and pestle, and then vortexed to ensure a homogeneous catalyst mixture. 0.35 g of this zeolite mixture (pelletized and sieved into 250-420 micrometer particles) were packed between quartz wool plugs and rested on the thermocouple in the middle of the furnace heating zone. Control reactions were performed with the same absolute loadings of the individual catalysts and catalyst beds were pelletized to the same size distribution. Void volume above and below the catalyst bed was filled with borosilicate glass beads to reduce homogeneous combustion. Blank reactors were loaded in the same manner in the absence of catalyst. For testing with increased catalyst loading a 304 stainless steel, O.D. 0.5 in, I.D. 0.40 in. reactor was used.

The flow of gases, including He (ultra-high purity, Airgas), 1% $O_2$ in He (ultra-high purity, Airgas), and $CH_4$ (research grade, Airgas) were controlled with independent mass flow controllers (Brooks instruments LLC). $H_2O$ (typically 3.2 kPa, the saturation vapor pressure at 298 K) was introduced into the gas stream via a stainless steel saturator and benzene was introduced using a syringe pump (Harvard Apparatus) with a heated liquid injection port. System pressure was controlled with a back pressure regulator (Equilibar U3L Series) between the reactor and the gas chromatograph. Stainless steel gas transfer lines were heated with resistive heating tape from the point of liquid injection until the gas chromatographic analysis unit. Typical reaction pretreatment involved calcining the catalyst at 823 K for 8 hours under 50 mL min$^{-1}$ dry air.

$CH_3OH$, dimethyl ether (DME), CO, $CO_2$, benzene, toluene, and xylene partial pressures evolved during catalytic tandem oxidation and alkylation reactions were quantified using a gas chromatograph (Agilent Technologies, 7890B). The gas chromatograph was equipped with a mechanizer, flame ionization detector, and thermal conductivity detector. Three columns were used for product separation: two HP-PLOT Q PT (30 m×0.53 mm×40 μm, Agilent #19095P-QO4PT) and HP PLOT Molsieve (30 m×0.53 mm×50 μm, Agilent #19095P-MS0E).

Reported values for selectivity and rates of product formation were averaged over three data points upon reaching steady-state.

Calibration curves for $CO_2$, $CH_3OH$, CO, and DME were constructed by flowing known mixtures of 1% $CO_2$/He, 0.5% $CH_3OH$/He, 90 ppm CO/$N_2$ or 10% DME/He and He, respectively, to a gas chromatograph. Calibration curves for benzene and toluene were constructed by injecting known liquid flow rates into a flowing gas stream of known flow rate. A response factor for xylene was inferred from that of toluene by carbon weighting.

The large partial pressure of $CH_4$ in the gas stream during catalytic $CH_4$ oxidation reactions prevented the accurate quantification of $CH_4$ consumption. As such, $CH_4$ conversion was assumed to be equal to the total molar flow rate of carbon of all observed products divided by the initial molar flow rate of $CH_4$:

$$X_{CH4} = \frac{\sum_{i=1}^{N} C_i F_i}{F_{CH4,0}}$$

where $X_{CH4}$ is the conversion of $CH_4$, $F_i$ is the molar flow rate of product i, $C_i$ is the number of carbon atoms incorporated from $CH_4$ into product i, $\Sigma C_i F_i$ is the total molar flow rate of carbon of all products, and $F_{CH4,0}$ is the initial molar flow rate of $CH_4$.

Product selectivity for catalytic $CH_4$ oxidation and tandem oxidation and alkylation was defined as:

$$S_i = \frac{C_i F_i}{\sum_{i=1}^{N} C_i F_i}$$

where $S_i$ is the selectivity of product i on a C-atom basis, $C_i$ is the number of carbon atoms incorporated from $CH_4$ into product i, $F_i$ is the molar flow rate of product i, and $\Sigma C_i F_i$ is the total molar flow rate of carbon of all products.

Product yield for catalytic $CH_4$ oxidation and tandem oxidation and alkylation was defined as:

$$Y_i = \frac{C_i F_i}{N_{Cu} \text{ or } g_{cat}}$$

where $Y_i$ is the selectivity of product i on a C-atom basis, $N_{Cu}$ is the number of moles of Cu within the zeolite determined by ICP, and $g_{cat}$ is the catalyst loading.

Example 4

The following example describes a $^{13}C_6H_6$ isotope switching experiment.

To quantify the contribution of benzene oxidation to the observed rates of CO and $CO_2$ formation, a $^{13}C_6H_6$ (Sigma Aldrich, 423637, 99 atom %) isotope switching experiment was completed. Prior to the experiment, the catalyst bed was calcined under 50 sccm dry air at 823 K for 8 hours before cooling to 543 K. At 543 K and 1 bar, reactant flows were introduced with unlabeled benzene until steady-state was attained. Steady state was tracked by gas chromatography and an online mass spectrometer (Hiden Analytical HPR-20/QIC). CO (m/z=28), $^{13}CO$ (m/z=29), $CO_2$ (m/z=44), $^{13}CO_2$ (m/z=45), benzene (m/z=78), and $^{13}C_6$ benzene (m/z=84) were tracked by mass spectrometry. Upon reaching steady-state, the benzene feed was switched to $^{13}C_6H_6$ until a steady-state was reached. The feed was then switched back to unlabeled benzene. The catalyst bed was then heated to 603 K and the same experiment was repeated. The rates of CO and $CO_2$ formation were unchanged with the change in benzene isotope. The change in the mass spectrum signal of each species was assumed to respond linearly to the gas phase concentration of each species. The natural abundance of $^{13}CO$ and $^{13}CO_2$ were accounted for in accounting for the contribution of benzene oxidation to the rates of CO and $CO_2$ formation as follows:

Prior to isotope switch:

$$x = \frac{^{12}CO \text{ signal}}{^{13}CO \text{ Signal}}$$

$$\text{Rate of } ^{13}CO \text{ formation pre-switch} = \frac{\text{Total Rate of } CO \text{ Formation}}{1 + x}$$

Following isotope switch:

$$y = \frac{^{12}CO \text{ signal}}{^{13}CO \text{ Signal}}$$

$$\text{Rate of } ^{13}CO \text{ formation post-switch} = \frac{\text{Total Rate of } CO \text{ Formation}}{1 + y}$$

Rate of $CO$ formation from benzene =

Rate of $^{13}CO$ formation post-switch −

Rate of $^{13}CO$ formation pre-switch

Fractional Contribution of Benzene =

$$\frac{\text{Rate of } CO \text{ formation from benzene}}{\text{Rate of } ^{12}CO \text{ formation pre-switch}}$$

Table 2 summarizes the contributions of benzene oxidation to the rates of CO and $CO_2$ formation and FIGS. 17A-18B present the MS signals.

TABLE 2

Percent contributions of $CH_4$ and $C_6H_6$ to observed rates of formation of CO and $CO_2$ at 543 and 603 K under tandem oxidation and alkylation reactions. (0.366 g Cu-CHA-2 + 1.097 g H-MFI-3), flow conditions: 78.3 sccm, $P_{CH4}$ = 17.8 kPa, $P_{C6H6}$ = 0.80 kPa, $P_{O2}$ = 0.09 kPa, $P_{H2O}$ = 3.1 kPa, bal He, atmospheric pressure.

| Temperature (K) | Source | CO | $CO_2$ |
|---|---|---|---|
| 543 | $CH_4$ | 15% | 81% |
|  | $C_6H_6$ | 85% | 19% |
| 603 | $CH_4$ | 15% | 58% |
|  | $C_6H_6$ | 85% | 42% |

Example 5

The following example describes an estimation of benzene oxidation across conditions.

Figure 16:
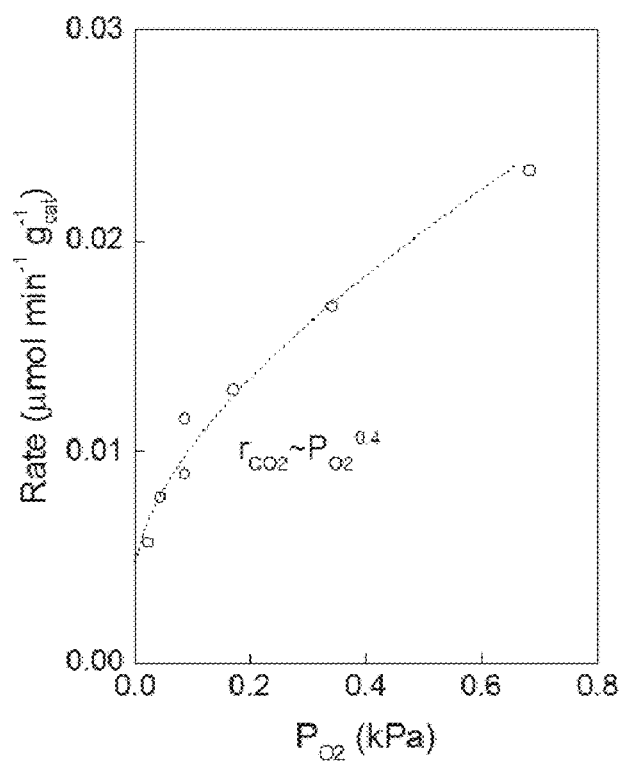
FIG. 16 shows, according to some embodiments, product formation rate dependence on $P_{O2}$ for benzene oxidation in the absence of $CH_4$.
Figure 17A:
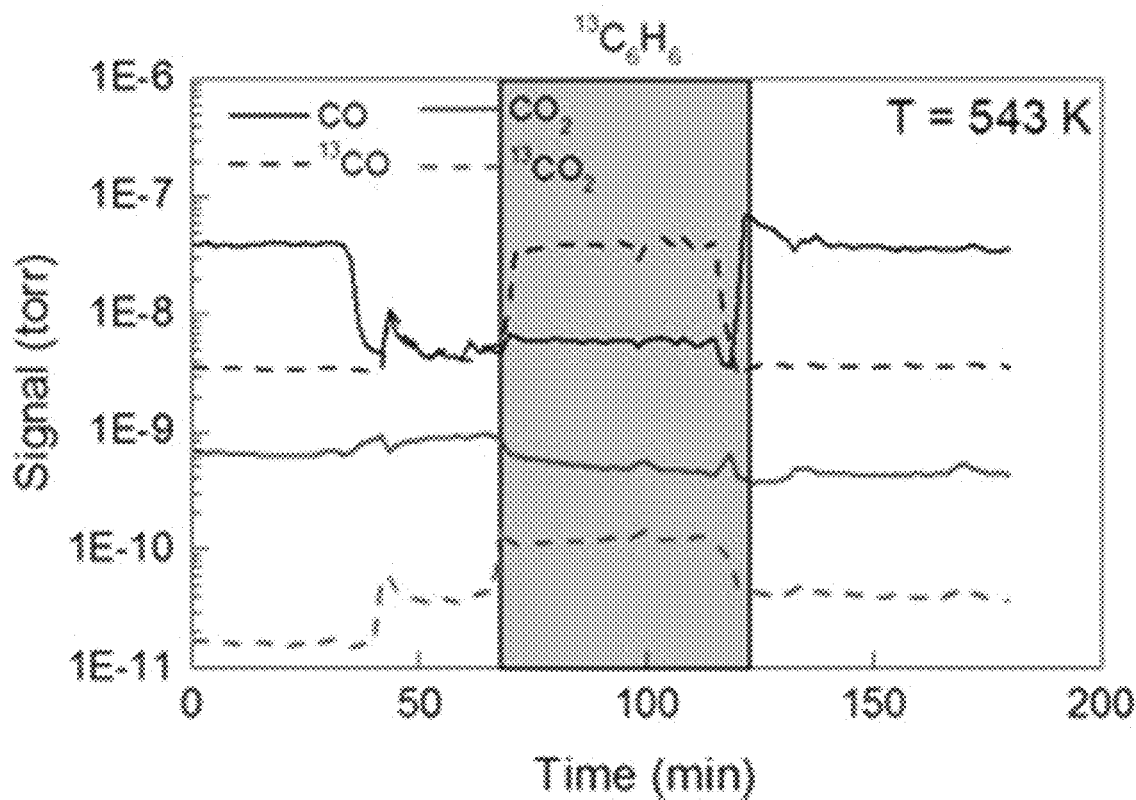
FIG. 17A shows, according to some embodiments, CO and $^{13}CO$ and $CO_2$ and $^{13}CO_2$ signals under tandem oxidation and alkylation conditions and upon the introduction of $^{13}C_6$ benzene at 543 K.
Figure 17B:
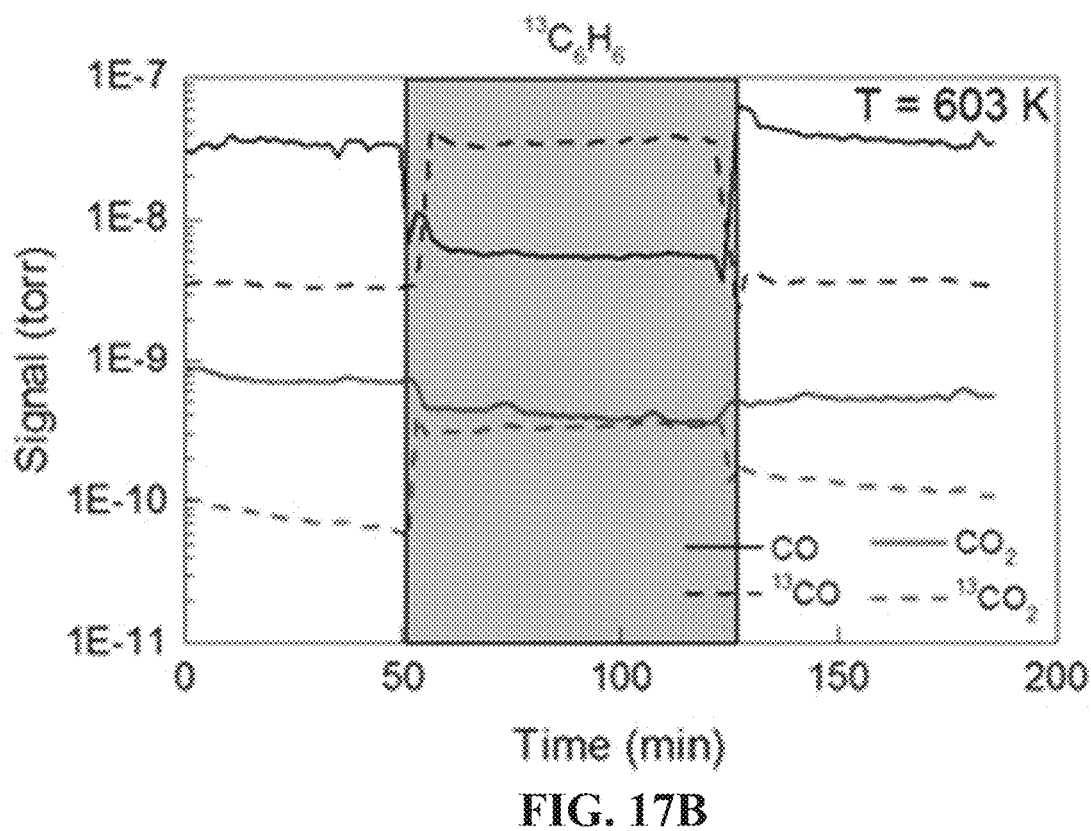
FIG. 17B shows, according to some embodiments, CO and $^{13}CO$ and $CO_2$ and $^{13}CO_2$ signals under tandem oxidation and alkylation conditions and upon the introduction of $^{13}C_6$ benzene at 603 K.
Figure 18A:
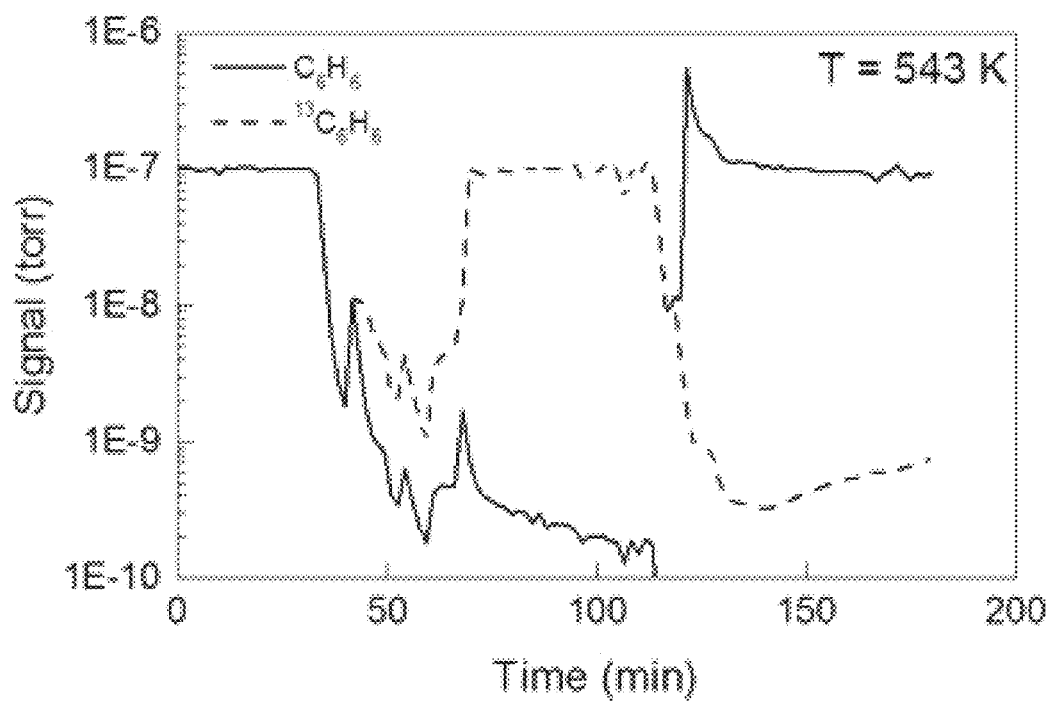
FIG. 18A shows, according to some embodiments, benzene and $^{13}C_6H_6$ signals under tandem oxidation and alkylation conditions and upon the introduction of $^{13}C_6$ benzene at 543 K
Figure 18B:
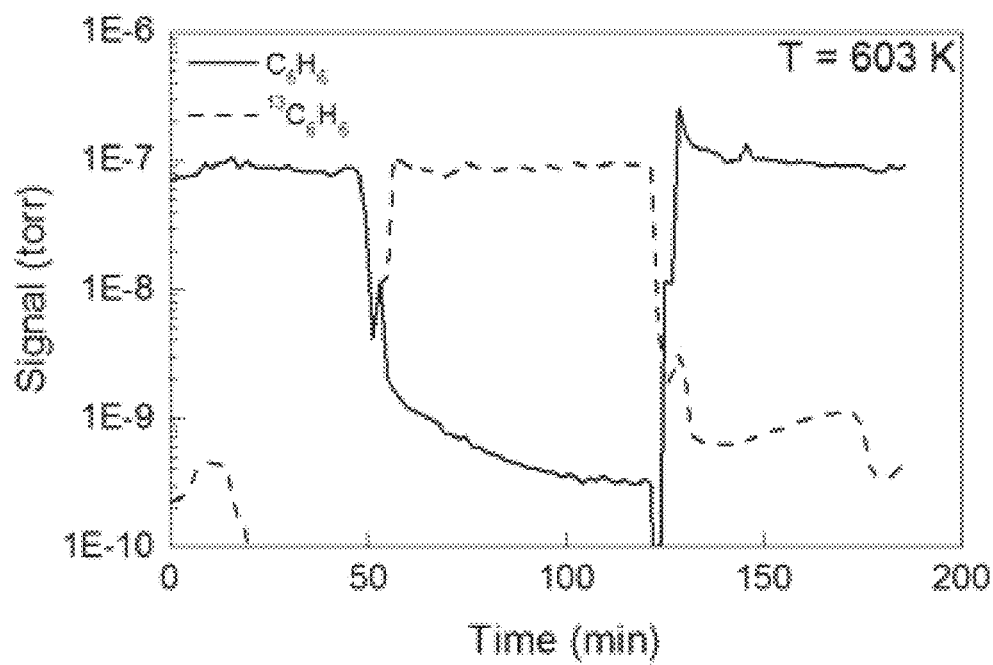
FIG. 18B shows, according to some embodiments, benzene and $^{13}C_6H_6$ signals under tandem oxidation and alkylation conditions and upon the introduction of $^{13}C_6$ benzene at 603 K.

Based on the observed rates of CO and $CO_2$ formation stemming from benzene at 543 and 603 K, 1 bar, estimates of the contribution of benzene oxidation to CO and $CO_2$ formation rates were obtained by using kinetic dependences and estimates of apparent activation energies, Estimates of apparent activation energies for CO and $CO_2$ formation from benzene were obtained from FIG. 4B. The apparent activation energy for CO was 45 kJ/mol and for $CO_2$ was 79 kJ/mol. It was demonstrated that the rate of $CO_2$, formation was independent of $P_{benzene}$ and the dependence of $CO_2$ formation from benzene on $P_{O2}$ is 0.4 order, as shown in FIG. 16. These dependences were assumed to hold for CO. These dependences along with the apparent activation energies allows for estimation of benzene oxidation rates across temperature and pressure. For FIG. 16, the catalyst composition and feed mixture was (0.2625 g Cu-CHA-1+0.7875 g H-MFI-1), 74.5 sccm, 543 K. $P_{O2}$=0.1 kPa, Pbenzene=0.80 kPa, $P_{H2O}$=3.1 kPa, bal He.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law. As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified, Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
    a first catalyst comprising a Cu-modified zeolite, wherein the first catalyst is capable of oxidizing a reactant comprising an optionally substituted alkane; and
    a second catalyst comprising a solid acid catalyst, wherein the second catalyst is capable of an alkylation and/or etherification coupling reaction between: (a) an intermediate comprising an optionally substituted saturated alcohol resulting from an oxidation of the reactant at the first catalyst; and (b) a co-reagent comprising an optionally substituted aromatic, alcohol, and/or alkene, and
    wherein the first catalyst comprises a plurality of cages and/or pores having an average characteristic dimension less than or equal to 5 angstroms such that a rate of diffusion of the co-reagent within one or more cages and/or pores of the first catalyst is lower than a rate of diffusion of the intermediate within the one or more cages and/or pores of the first catalyst, and
    wherein the composition further comprises an oxidizing agent.

2. The composition of claim 1, wherein the rate of diffusion of the co-reagent within the one or more cages and/or pores of the first catalyst is no more than 60% the rate diffusion of the intermediate within the one or more cages and/or pores of the first catalyst.

3. The composition of claim 1, wherein the rate of diffusion of the co-reagent within the one more cages and/or pores of the first catalyst is no more than 20% the rate diffusion of the intermediate within the one or more cages and/or pores of the first catalyst.

4. The composition of claim 1, wherein the rate of diffusion of the co-reagent within the one or more cages and/or pores of the first catalyst is no more than 10% the rate diffusion of the intermediate within the one or more cages and/or pores of the first catalyst.

5. The composition of claim 1, wherein the rate of diffusion of the co-reagent within the one or more cages and/or pores of the first catalyst is no more than 1% the rate diffusion of the intermediate within the one or more cages and/or pores of the first catalyst.

6. The composition of claim 1, wherein the first catalyst comprises Cu-modified SSZ-13, AEI, AFX, MAZ, and/or mixtures thereof.

7. The composition of claim 1, wherein the first catalyst comprises Cu-modified SSZ-13.

8. The composition of claim 1, wherein the second catalyst comprises a zeolite, a metal oxide, a metal-organic-framework (MOF), a polyoxometallate, sulfated zirconia, and/or mixtures thereof.

9. The composition of claim 8, wherein the metal oxide comprises alumina and/or silica.

10. The composition of claim 8, wherein the metal oxide comprises molybdenum oxide and/or tungsten oxide.

11. The composition of claim 10, wherein the metal oxide is supported by aluminosilicate.

12. The composition of claim 1, wherein the second catalyst comprises ZSM-5, ZSM-22, NU-87, SSZ-33, beta, and/or mixtures thereof.

13. The composition of claim 12, wherein the second catalyst comprises ZSM-5.

14. The composition of claim 1, wherein the oxidizing agent comprises dioxygen ($O_2$), ozone ($O_3$), nitric oxide, nitrous oxide, hydrogen peroxide, and/or combinations thereof.

15. The composition of claim 1, wherein the reactant comprises methane, ethane, propane, butane, and/or combinations thereof.

16. The composition of claim 1, wherein the intermediate comprises methanol, ethanol, propanol, butanol, and/or combinations thereof.

17. The composition of claim 1, wherein the co-reagent comprises benzene, naphthalene, anthracene, toluene, ethylbenzene, phenol, aniline, acetophenone, benzaldehyde, benzoic acid, benzonitrile, xylene, mesitylene, durene, styrene, biphenyl, benzyl alcohol, cyclohexene, cyclohexanol, cyclohexanone, hexene, butene, and/or combinations thereof.

18. The composition of claim 1, wherein the first catalyst and the second catalyst are comprised as a powder mixture.

19. The composition of claim 18, wherein the powder mixture is a pelletized powder mixture.

20. The composition of claim 1, wherein a weight ratio of the first catalyst to the second catalyst is greater than or equal to 0.1:1 and less than or equal to 1:1.

* * * * *